(12) United States Patent
Frank et al.

(10) Patent No.: US 6,284,881 B1
(45) Date of Patent: *Sep. 4, 2001

(54) FELINE FC EPSILON RECEPTOR ALPHA CHAIN NUCLEIC ACID MOLECULES

(75) Inventors: Glenn R. Frank, Wellington; James P. Porter, Fort Collins; Keith E. Rushlow, Fort Collins; Donald L. Wassom, Fort Collins; Eric R. Weber, Fort Collins, all of CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/515,431

(22) Filed: Feb. 29, 2000

Related U.S. Application Data

(62) Division of application No. 09/005,299, filed on Jan. 9, 1998, now Pat. No. 6,103,494, which is a division of application No. 08/768,964, filed on Dec. 19, 1996, now Pat. No. 5,958,880.

(51) Int. Cl.[7] ............................ C12N 15/12; C12N 15/63; C12N 15/70; C12N 15/85; C12P 21/02
(52) U.S. Cl. ..................... 536/23.5; 536/23.1; 435/455; 435/471; 435/252.3; 435/320.1; 435/69.1
(58) Field of Search ................................ 536/23.1, 23.5; 435/6, 69.1, 471, 252.3, 320.1, 455

(56) References Cited

U.S. PATENT DOCUMENTS

| | | |
|---|---|---|
| 4,962,035 | 10/1990 | Leder et al. . |
| 6,103,494 | * 8/2000 | Frank et al. . |

FOREIGN PATENT DOCUMENTS

| | | |
|---|---|---|
| 0 259 615 | 3/1988 | (EP) . |
| 51113443 | 5/1993 | (JP) . |
| WO 90/04640 | 5/1990 | (WO) . |
| WO 91/06570 | 5/1991 | (WO) . |

OTHER PUBLICATIONS

Meinkoth et al. Analytical Biochemistry 138:267–284 (1984).*

Voet and Voet. In Biochemistry. John Wiley& Sons, Inc. (1990) vol. 1, pp. 126–127 and 228–230.*

Hayashi, et al., Genbank Accession No. D16413, submitted Jun. 8, 1993.

Kochan, et al., "Isolation of the Gene Coding for the Alpha Subunit of the Human High Affinity IgE Receptor," (1988) *Nucleic Acids Res. 16(8)*, p. 3584.

Küster, et al., "Characterization and Expression of the Gene for the Human Fc Receptor γ Subunit," (1990) *J. Biol. Chem. 265(11)*, pp. 6448–6452.

Küster, et al., "The Gene and cDNA for the Human High Affinity Immunoglobulin E Receptor β Chain and Expression of the Complete Human Receptor," (1992) *J. Biol. Chem. 267(18)*, pp. 12782–12787.

Lowenthal, et al., "Passive Transfer of IgE–Mediated Cutaneous Reactivity in Heterologous Species," (1993) *Annals of Allergy 71*, 481–484.

Pang, et al., "Characterization of the Gene for the Human High Affinity IgE Receptor (FcεRI) α–Chain," (1993) *J. Immunol. 151(11)*, pp. 6166–6174.

Shimizu, et al., "Human and Rat Mast Cell High–Affintiy Immunoglobulin E Receptors: Characterization of Putative α–Chain Gene Products,"(1988), *Proc. Natl. Acad. Sci. USA (85)*, pp. 1907–1911.

George, et al., "Current Methods in Sequence Comparison and Analysis," (1988)*Macromolecular Sequencing and Synthesis Selected Methods and Applications* pp. 127–149.

* cited by examiner

*Primary Examiner*—Phillip Gambel
*Assistant Examiner*—Jessica H. Roark
(74) *Attorney, Agent, or Firm*—Heska Corporation

(57) ABSTRACT

The present invention relates to feline Fc epsilon receptor alpha chain nucleic acid molecules, compositions comprising such nucleic acid molecules, and methods to use such nucleic acid molecules to produce feline Fc epsilon receptor alpha chain proteins.

17 Claims, No Drawings

FELINE FC EPSILON RECEPTOR ALPHA CHAIN NUCLEIC ACID MOLECULES

This Application is a Divisional Application of application Ser. No. 09/005,299, filed Jan. 9, 1998, which issued as U.S. Pat. No. 6,103,494 on Aug. 15, 2000, which is a Divisional of application Ser. No. 08/768,964, filed Dec. 19, 1996, and which issued as U.S. Pat. No. 5,958,880 on Sep. 28, 1999, entitled "NOVEL FELINE Fc EPSILON RECEPTOR ALPHA CHAIN PROTEINS, NUCLEIC ACID MOLECULES AND USES THEREOF", which is incorporated herein by this reference in its entirety.

FIELD OF THE INVENTION

The present invention relates to feline Fc epsilon receptor alpha chain nucleic acid molecules, proteins encoded by such nucleic acid molecules, antibodies raised against such proteins, and inhibitors of such proteins. The present invention also includes methods to detect IgE using such proteins and antibodies.

BACKGROUND OF THE INVENTION

Diagnosis of disease and determination of treatment efficacy are important tools in medicine. IgE antibody production in an animal can be indicative of disease including, for example, allergy, atopic disease, hyper IgE syndrome, internal parasite infections and B cell neoplasia. In addition, detection of IgE production in an animal following a treatment is indicative of the efficacy of the treatment, such as when using treatments intended to disrupt IgE production.

Immunological stimulation can be mediated by IgE antibodies when IgE complexes with Fc epsilon receptors. Fc epsilon receptors are found on the surface of certain cell types, such as mast cells. Mast cells store biological mediators including histamine, prostaglandins and proteases. Release of these biological mediators is triggered when IgE antibodies complex with Fc epsilon receptors on the surface of a cell. Clinical symptoms result from the release of the biological mediators into the tissue of an animal.

Until the discovery of the present invention, detection of IgE in samples obtained from animals has been hindered by the absence of suitable reagents for detection of IgE. Various compounds have been used to detect IgE in IgE-containing compositions. In particular, antibodies that bind selectively to epsilon idiotype antibodies (i.e., anti-IgE antibodies) have been used to detect IgE. These anti-IgE antibodies, however, can cross-react with other antibody idiotypes, such as gamma isotype antibodies. Also, creation of reagents capable of inhibiting the activity of Fc epsilon receptors has been limited.

The discovery of the present invention includes a novel feline Fc epsilon receptor alpha chain (FcεRα) protein and the use of such a protein to detect the presence of IgE in a putative IgE-containing composition; to identify inhibitors of biological responses mediated by a feline FcεRα protein; and as a therapeutic compound to prevent or treat clinical symptoms that result from feline FcεRα-mediated biological responses. When used in an assay to detect IgE, a feline FcεRα protein provides an advantage over, for example anti-IgE antibodies, to detect IgE because a feline FcεRα protein can bind to an IgE with more specificity (i.e., less idiotype cross-reactivity) and more sensitivity (i.e., affinity) than anti-IgE binding antibodies.

Prior investigators have disclosed the nucleic acid sequence for: the human FcεR alpha chain (Kochan et al., *Nucleic Acids Res.* 16:3584, 1988; Shimizu et al., *Proc. Natl. Acad. Sci. USA* 85:1907–1911, 1988; and Pang et al., *J. Immunol.* 151:6166–6174, 1993); the human FcεR beta chain (Kuster et al., *J. Biol. Chem.* 267:12782–12787, 1992); the human FcεR gamma chain (Kuster et al., *J. Biol. Chem.* 265:6448–6452, 1990); and the canine FcεR alpha chain (GenBank™ accession number D16413). Although the subunits of human FcεR have been known as early as 1988, they have never been used to identify a feline FcεR. Similarly, even though the canine FcεR chain has been known since 1993, it has never been used to identify a feline FcεR. Moreover, the determination of human and canine Fc epsilon receptor sequences does not indicate, suggest or predict the cloning of a novel FcεRα gene from a different species, in particular, from a feline species.

Thus, products and processes of the present invention are needed in the art that will provide specific detection of IgE and treatment of Fc epsilon receptor-mediated disease.

SUMMARY OF THE INVENTION

The present invention relates to a novel product and process for detecting IgE and protecting animals from Fc epsilon receptor-mediated biological responses. According to the present invention there are provided feline FcεRα proteins and mimetopes thereof; feline FcεRα nucleic acid molecules, including those that encode such proteins; antibodies raised against such feline FcεRα proteins (i.e., anti-feline FcεRα antibodies); and other compounds that inhibit the ability of feline FcεRα protein to form a complex with IgE (i.e, inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to Fc epsilon receptor-mediated biological responses.

One embodiment of the present invention is an isolated nucleic acid molecule encoding a feline FcεRα protein. The feline FcεRα protein preferably includes: proteins comprising amino acid sequences SEQ ID NO:2, SEQ ID NO:7, SEQ ID NO: 12 and SEQ ID NO:13; and proteins encoded by allelic variants of a nucleic acid molecules encoding a protein comprising any of the amino acid sequences. Particularly preferred feline FcεRα nucleic acid molecules include: nucleic acid molecules comprising nucleic acid sequences SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and SEQ ID NO:16; and nucleic acid molecules comprising allelic variants of nucleic acid molecules comprising nucleic acid sequences SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO: 15 and SEQ ID NO:16.

The present invention also includes an isolated feline FcεRα protein. A preferred feline FcεRα protein is encoded by a nucleic acid molecule that hybridizes under stringent hybridization conditions to a nucleic acid sequence including SEQ ID NO:3, SEQ ID NO:5, SEQ ID NO:8, SEQ ID NO:15 and SEQ ID NO:16. Particularly preferred feline FcεRα proteins include at least one of the following amino acid sequences: SEQ ID NO:2, SEQ ID NO:7, SEQ ID NO:12 and SEQ ID NO:13.

The present invention also relates to recombinant molecules, recombinant viruses and recombinant cells that include feline FcεRα nucleic acid molecules of the present invention. Also included are methods to produce such nucleic acid molecules, recombinant molecules, recombinant viruses and recombinant cells.

The present invention also includes detection methods and kits that detect IgE. One embodiment of the present invention is a method to detect IgE comprising: (a) contacting an isolated feline FcεRα molecule with a putative IgE-containing composition under conditions suitable for formation of a FcεRα molecule:IgE complex; and (b) determining the presence of IgE by detecting the FcεRα molecule:IgE complex, the presence of the FcεRα molecule:IgE complex indicating the presence of IgE. A preferred feline FcεRα molecule is one which a carbohydrate group of the feline FcεRα molecule is conjugated to biotin.

Another embodiment of the present invention is a method to detect IgE comprising: (a) contacting a recombinant cell with a putative IgE-containing composition under conditions suitable for formation of a recombinant cell:IgE complex, in which the recombinant cell comprises a feline FcεRα molecule; and (b) determining the presence of IgE by detecting the recombinant cell:IgE complex, the presence of the recombinant cell:IgE complex indicating the presence of IgE. A preferred method to detect IgE comprises: (a) immobilizing the FcεRα molecule on a substrate; (b) contacting the FcεRα molecule with the putative IgE-containing composition under conditions suitable for formation of a FcεRα molecule:IgE complex bound to the substrate; (c) removing non-bound material from the substrate under conditions that retain FcεRα molecule:IgE complex binding to the substrate; and (d) detecting the presence of the FcεRα molecule:IgE complex. Another preferred method to detect IgE comprises: (a) immobilizing a specific antigen on a substrate; (b) contacting the antigen with the putative IgE-containing composition under conditions suitable for formation of an antigen:IgE complex bound to the substrate; (c) removing non-bound material from the substrate under conditions that retain antigen:IgE complex binding to said substrate; and (d) detecting the presence of the antigen:IgE complex by contacting the antigen:IgE complex with said FcεRα molecule. Another preferred method to detect IgE comprises: (a) immobilizing an antibody that binds selectively to IgE on a substrate; (b) contacting the antibody with the putative IgE-containing composition under conditions suitable for formation of an antibody:IgE complex bound to the substrate; (c) removing non-bound material from the substrate under conditions that retain antibody:IgE complex binding to the substrate; and (d) detecting the presence of the antibody:IgE complex by contacting the antibody:IgE complex with said FcεRα molecule. Another preferred method to detect IgE comprises: (a) immobilizing a putative IgE-containing composition on a substrate; (b) contacting the composition with the FcεRα molecule under conditions suitable for formation of a FcεRα molecule:IgE complex bound to the substrate; (c) removing non-bound material from the substrate under conditions that retain FcεRα molecule:IgE complex binding to the substrate; and (d) detecting the presence of the FcεRα molecule:IgE complex Another embodiment of the present invention is a method to detect flea allergy dermatitis comprising: (a) immobilizing a flea allergen on a substrate; (b) contacting the flea allergen with a putative IgE-containing composition under conditions suitable for formation of an allergen:IgE complex bound to the substrate; (c) removing non-bound material from the substrate under conditions that retain allergen:IgE complex binding to the substrate; and (d) detecting the presence of the allergen:IgE complex by contacting said allergen:IgE complex with a feline FcεRα protein. Preferably, the flea allergen is a flea saliva antigen and more preferably flea saliva products and/or flea saliva proteins.

The present invention also includes a kit for performing methods of the present invention. One embodiment is a kit for detecting IgE comprising a feline FcεRα protein and a means for detecting IgE. Another embodiment is a kit for detecting flea allergy dermatitis comprising a feline FcεRα protein and a flea allergen.

The present invention also includes an inhibitor that interferes with formation of a complex between feline FcεRα protein and IgE, in which the inhibitor is identified by its ability to interfere with the complex formation. A particularly preferred inhibitor includes a substrate analog of a feline FcεRα protein, a mimetope of a feline FcεRα protein and a soluble portion of a feline FcεRα protein. Also included is a method to identify a compound that interferes with formation of a complex between feline FcεRα protein and IgE, the method comprising: (a) contacting an isolated feline FcεRα protein with a putative inhibitory compound under conditions in which, in the absence of the compound, the feline FcεRα protein forms a complex with IgE; and (b) determining if the putative inhibitory compound inhibits the complex formation. A test kit is also includes to identify a compound capable of interfering with formation of a complex between a feline FcεRα protein and IgE, the test kit comprising an isolated feline FcεRα protein that can complex with IgE and a means for determining the extent of interference of the complex formation in the presence of a putative inhibitory compound.

Yet another embodiment of the present invention is a therapeutic composition that is capable of reducing Fc epsilon receptor-mediated biological responses. Such a therapeutic composition includes one or more of the following therapeutic compounds: an isolated feline FcεRα protein; a mimetope of a feline FcεRα protein; an isolated nucleic acid molecule that hybridizes under stringent hybridization conditions with a feline FcεRα gene; an isolated antibody that selectively binds to a feline FcεRα protein; and an inhibitor that interferes with formation of a complex between a feline FcεRα protein and IgE. A method of the present invention includes the step of administering to an animal a therapeutic composition of the present invention.

Yet another embodiment of the present invention is a method to produce a feline FcεRα protein, the method comprising culturing a cell transformed with a nucleic acid molecule encoding a feline FcεRα protein.

DETAILED DESCRIPTION OF THE INVENTION

The present invention provides for isolated feline Fc epsilon receptor alpha chain (FcεRα) proteins, isolated feline FcεRα nucleic acid molecules, antibodies directed against feline FcεRα proteins and other inhibitors of feline FcεRα activity. As used herein, the terms isolated feline FcεRα proteins and isolated feline FcεRα nucleic acid molecules refers to feline FcεRα proteins and feline FcεRα nucleic acid molecules derived from cats and, as such, can be obtained from their natural source or can be produced using, for example, recombinant nucleic acid technology or chemical synthesis. Also included in the present invention is the use of these proteins and antibodies in a method to detect epsilon immunoglobulin (referred to herein as IgE or IgE antibody) as well as in other applications, such as those disclosed below. The products and processes of the present invention are advantageous because they enable the detection of IgE and the inhibition of IgE or feline FcεRα protein activity associated with disease. As used herein, feline Fc epsilon alpha chain receptor protein can be referred to as FcεRα protein or FcεRα chain protein.

One embodiment of the present invention is an isolated protein comprising a feline FcεRα protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated feline FcεRα protein can be a full-length protein or any homolog of such a protein. As used herein, a protein can be a polypeptide or a peptide. Preferably, a feline FcεRα protein comprises at least a portion of a feline FcεRα protein that binds to IgE, i.e., that is capable of forming a complex with an IgE.

A feline FcεRα protein of the present invention, including a homolog, can be identified in a straight-forward manner by the protein's ability to bind to IgE. Examples of feline FcεRα protein homologs include feline FcεRα proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog is capable of binding to IgE.

Feline FcεRα protein homologs can be the result of natural allelic variation or natural mutation. Feline FcεRα protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated feline FcεRα proteins of the present invention have the further characteristic of being encoded by nucleic acid molecules that hybridize under stringent hybridization conditions to a gene encoding a feline FcεRα protein. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety. Briefly, at page 269, column 1, Meinkoth et al. teach the following: "The formation of nucleic acid hybrids is a reversible process and an understanding of the parameters which affect their stability enable one to derive the optimal conditions for discriminating between perfect and imperfect hybrids. The melting temperature ($T_m$) is affected by ionic strength (M, in mol/liter), base composition (% G+C), the length of the shortest chain in the duplex (n), and the concentration of helix destabilizing agents such as formamide. The following equation has been derived from analyzing the influence of these factors on hybrid stability:

$$T_m = 81.5° C. + 16.6 \log M + 0.41 (\% G+C) - 500/n - 0.61(\% \text{ formamide}).$$

This equation pertains to probes longer than approximately 50 nucleotides. Hybrids between oligonucleotides (14–20 bp) and immobilized DNA show decreased stability and an empirical formula has been determined to define the optimal conditions for their hybridization. The temperature at which 50% of these short duplexes dissociate ($T_d$) when the hybridization is performed under standard conditions (e.g., 0.9 M NaCl) is:

$$T_d(° C.) = 4(G+C) + 2(A+T)$$

where G, C, A, and T indicate the number of the corresponding nucleotides in the oligomer. A temperature 5° below the $T_d$ is used to detect hybridization between perfectly matched molecules.

The stability of duplexes formed between strands with mismatched bases is decreased according to the number and location of the mismatches and is especially pronounced for short (e.g., 14 bp) oligonucleotides. For hybrids longer than 150 bp, the $T_m$ of a DNA duplex decreases by 1° C. with every 1% of base pairs which are mismatched. For hybrids shorter than 20 bp, the $T_m$ decreases by approximately 5° C. for every mismatched base pair. In order to minimize the hybridization of probe to related but nonidentical sequences, hybridization reactions must be performed under the most stringent conditions possible. From the discussion above, hybridization stringency can be altered by adjusting the salt and/or formamide concentrations and/or by changing the temperature. The stringency can be adjusted either during the hybridization step, or in the posthybridization washes. It is often convenient to perform the hybridization at low stringencies and wash at increasing stringencies, analyzing the results after each wash. This enables the detection of related sequences and the monitoring of the effectiveness of the washes in removing these sequences. This strategy also enables one to obtain an estimate of sequence relatedness."

As used herein, a feline FcεRα gene includes all nucleic acid sequences related to a natural feline FcεRα gene such as regulatory regions that control production of the feline FcεRα protein encoded by that gene (such as, but not limited to, transcription, translation or post-translation control regions) as well as the coding region itself. In one embodiment, a feline FcεRα gene of the present invention includes nucleic acid sequence SEQ ID NO:1, SEQ ID NO:3, SEQ ID NO:4, SEQ ID NO:5, SEQ ID NO:6, SEQ ID NO:8, SEQ ID NO:11, SEQ ID NO:14 and/or SEQ ID NO:15. Nucleic acid sequence SEQ ID NO:1 represents the deduced sequence of the coding strand of a complementary DNA (cDNA) nucleic acid molecule denoted herein as nfelFcεRα$_{1069}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

It should be noted that since nucleic acid sequencing technology is not entirely error-free, SEQ ID NO:1 and SEQ ID NO:3 (as well as other nucleic acid and protein sequences presented herein) represent apparent nucleic acid sequences of certain nucleic acid molecules encoding feline FcεRα proteins of the present invention.

In another embodiment, a feline FcεRα gene can be an allelic variant that includes a similar but not identical sequence to SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and/or SEQ ID NO:16. An allelic variant of a feline FcεRα gene is a gene that occurs at essentially the same locus (or loci) in the genome as the gene including SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and/or SEQ ID NO:16, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given cat since the genome is diploid and/or among a group of two or more cats. The present invention also includes variants due to laboratory manipulation, such as, but not limited to, variants produced during polymerase chain reaction amplification.

The minimal size of a FcεRα protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a feline FcεRα protein homolog of the present invention is from about 12 to about 18 nucleotides in length. Thus, the minimal size of a feline FcεRα protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired. Preferably, the preferred size of a protein encoded by a nucleic acid molecule of the present invention is a portion of the protein that binds to IgE which is about 30 amino acids, more preferably about 35 amino acids and even more preferably about 44 amino acids in length.

As used herein, a feline refers to any member of the cat family, including domestic cats, wild cats and zoo cats. Examples of cats from which to isolate feline FcεRα proteins of the present invention (including isolation of the natural protein or production of the protein by recombinant or synthetic techniques) include, but are not limited to, domestic cats, lions, tigers, leopards, panthers, cougars, bobcats, lynx, jaguars, cheetahs, and servals, with domestic cats being more preferred and *Felis domesticus* cats being even more preferred.

Suitable cat cells from which to isolate a feline FcεRα protein of the present invention include cells that have FcεR proteins. Preferred cat cells from which to obtain a feline FcεRα protein of the present invention include basophil cells, mast cells, mastocytoma cells, dendritic cells, B lymphocytes, macrophages, eosinophils, and/or monocytes. A feline FcεRα of the present invention is preferably obtained from mastocytoma cells, mast cells or basophil cells.

The present invention also includes mimetopes of feline FcεRα proteins of the present invention. As used herein, a mimetope of a feline FcεRα protein of the present invention refers to any compound that is able to mimic the activity of such a feline FcεRα protein (e.g., ability to bind to IgE), often because the mimetope has a structure that mimics the feline FcεRα protein. It is to be noted, however, that the mimetope need not have a structure similar to a feline FcεRα protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; andlor any other peptidomimetic compounds. Mimetopes of the present invention can be designed using computer-generated structures of feline FcεRα proteins of the present invention. Mimetopes can also be obtained by generating random samples of molecules, such as oligonucleotides, peptides or other organic molecules, and screening such samples by affinity chromatography techniques using the corresponding binding partner, (e.g., a feline IgE Fc domain or anti-feline FcεRα antibody). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of feline FcεRα mimetopes include anti-idiotypic antibodies, oligonucleotides produced using Selex™ technology, peptides identified by random screening of peptide libraries and proteins identified by phage display technology. A preferred mimetope is a peptidomimetic compound that is structurally and/or functionally similar to a feline FcεRα protein of the present invention, particularly to the IgE Fc domain binding site of the feline FcεRα protein. As used herein, the Fc domain of an antibody refers to the portion of an immunoglobulin that has Fc receptor binding effector function. Typically, the Fc domain of an IgE comprises the CH2 and CH3 domains of the heavy chain constant region.

According to the present invention, a feline FcεRα molecule of the present invention refers to: a feline FcεRα protein, in particular a soluble feline FcεRα protein; a feline FcεRα homolog; a feline FcεRα mimetope; a feline FcεRα substrate analog; or a feline FcεRα peptide. Preferably, a feline FcεRα molecule binds to IgE.

One embodiment of a feline FcεRα protein of the present invention is a fusion protein that includes a feline FcεRα protein-containing domain attached to one or more fusion segments. Suitable fusion segments for use with the present invention include, but are not limited to, segments that can: enhance a protein's stability; act as an immunopotentiator to enhance an immune response against a feline FcεRα protein; and/or assist purification of a feline FcεRα protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the feline FcεRα-containing domain of the protein and can be susceptible to cleavage in order to enable straight-forward recovery of a feline FcεRα protein. Fusion proteins are preferably produced by culturing a recombinant cell transformed with a fusion nucleic acid molecule that encodes a protein including the fusion segment attached to either the carboxyl and/or amino terminal end of a feline FcεRα-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of β-galactosidase, a strep tag peptide, other domains that can be purified using compounds that bind to the domain, such as monoclonal antibodies); and/or a linker and enzyme domain (e.g., alkaline phosphatase domain connected to a feline FcεRα protein by a linker). More preferred fusion segments include metal binding domains, such as a poly-histidine segment; a maltose binding domain; a strep tag peptide, such as that available from Biometra in Tampa, Fla.; and a phage T7 S10 peptide.

A preferred feline FcεRα protein of the present invention is encoded by a nucleic acid molecule that hybridizes under stringent hybridization conditions with at least one of the following nucleic acid molecules: $nfelFc_\epsilon R\alpha_{1069}$, $nfelFc_\epsilon R\alpha_{789}$, $nfelFc_\epsilon R\alpha_{714}$, $nfelFc_\epsilon R\alpha_{597}$ and $nfelFc_\epsilon R\alpha_{522}$. Preferably, the feline FcεRα protein binds to IgE. A further preferred isolated protein is encoded by a nucleic acid molecule that hybridizes under stringent hybridization conditions with a nucleic acid molecule having nucleic acid sequence SEQ ID NO:3, SEQ ID NO:5, SEQ ID NO:8, SEQ ID NO:15 and SEQ ID NO:16.

Translation of SEQ ID NO:1 suggests that nucleic acid molecule $nfelFc_\epsilon R\alpha_{1069}$ encodes a full-length feline protein of about 263 amino acids, referred to herein as $PfelFc_\epsilon R\alpha_{263}$, represented by SEQ ID NO:2, assuming an open reading frame having an initiation (start) codon spanning from about nucleotide 65 through about nucleotide 67 of SEQ ID NO:1 and a termination (stop) codon spanning from about nucleotide 854 through about nucleotide 856 of SEQ ID NO:1. The coding region encoding $PfelFc_\epsilon R\alpha_{263}$ is represented by nucleic acid molecule $nfelFc_\epsilon R\alpha_{789}$, having a coding strand with the nucleic acid sequence represented by SEQ ID NO:4 and a complementary strand with the nucleic acid sequence represented by SEQ ID NO:5. Analysis of SEQ ID NO:2 suggests the presence of a signal peptide encoded by a stretch of amino acids spanning from about amino acid 1 through about amino acid 25. The proposed mature protein, denoted herein as $PfelFc_\epsilon R\alpha_{238}$, contains about 238 amino acids which is represented herein as SEQ ID NO:7. $PfelFc_\epsilon R\alpha_{238}$ is encoded by nucleic acid molecule $nfelFc_\epsilon R\alpha_{714}$, having a coding strand with the nucleic acid sequence represented by SEQ ID NO:6 and a complementary strand with the nucleic acid sequence represented by SEQ ID NO:8. The amino acid sequence of $PfelFc_\epsilon R\alpha_{238}$ (i.e. SEQ ID NO:7) predicts that $PfelFc_\epsilon R\alpha_{238}$ has an estimated molecular weight of about 30.2 kD, an estimated pI of about 9.51.

Comparison of amino acid sequence SEQ ID NO:2 (i.e., the amino acid sequence of $PfelFc\epsilon R\alpha_{263}$) with amino acid sequences reported in GenBank™ indicates that SEQ ID NO:2 showed the most homology, i.e., about 54% identity, with a Fc epsilon receptor alpha chain protein of *Homo Sapiens* (GenBank accession number J03605).

More preferred feline FcεRα proteins of the present invention include proteins comprising amino acid sequences that are at least about 60%, preferably at least about 65%, more preferably at least about 70%, more preferably at least about 75%, more preferably at least about 80% and even more preferably at least about 85%, identical to amino acid sequence SEQ ID NO:2, SEQ ID NO:7, SEQ ID NO:12 and/or SEQ ID NO:13.

More preferred feline FcεRα proteins of the present invention include proteins encoded by a nucleic acid molecule comprising at least a portion of $nfelFc_\epsilon R\alpha_{1069}$, $nfelFc_\epsilon R\alpha_{789}$, $nfelFc_\epsilon R\alpha_{714}$, $nfelFc_\epsilon R\alpha_{597}$ and $nfelFc_\epsilon R\alpha_{522}$, or of allelic variants of such nucleic acid molecules, the portion being capable of binding to IgE. More preferred is a feline FcεRα protein encoded by $nfelFc_\epsilon R\alpha_{1069}$, $nfelFc_\epsilon R\alpha_{789}$, $nfelFc_\epsilon R\alpha_{714}$, $nfelFc_\epsilon R\alpha_{597}$ and $nfelFc_{\epsilon R\alpha 522}$, or by an allelic variant of such nucleic acid molecules. Particularly preferred feline FcεRα proteins are $PfelFc_\epsilon R\alpha_{238}$, $PfelFc_\epsilon R\alpha_{263}$, $PfelFc_\epsilon R\alpha_{199}$ and $PfelFc_\epsilon R\alpha_{174}$.

In one embodiment, a preferred feline FcεRα protein of the present invention is encoded by at least a portion of SEQ ID NO:1, SEQ ID NO:4, SEQ ID NO:6, SEQ ID NO:11 and/or SEQ ID NO:14, and, as such, has an amino acid sequence that includes at least a portion of SEQ ID NO:2, SEQ ID NO:7, SEQ ID NO:12 and/or SEQ ID NO:13.

Also preferred is a feline FcεRα protein encoded by an allelic variant of a nucleic acid molecule comprising at least a portion of SEQ ID NO:1, SEQ ID NO:4, SEQ ID NO:6, SEQ ID NO:11 and/or SEQ ID NO:14. Particularly preferred feline FcεRα proteins of the present invention include SEQ ID NO:2, SEQ ID NO:7, SEQ ID NO:12 and SEQ ID NO:13 (including, but not limited to, the proteins consisting of such sequences, fusion proteins and multivalent proteins) and proteins encoded by allelic variants of nucleic acid molecules that encode SEQ ID NO:2, SEQ ID NO:7, SEQ ID NO:12 and/or SEQ ID NO:13.

Another embodiment of the present invention is an isolated nucleic acid molecule that hybridizes under stringent hybridization conditions with a feline FcεRα gene. The identifying characteristics of such a gene are heretofore described. A nucleic acid molecule of the present invention can include an isolated natural feline FcεRα gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a feline FcεRα gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated feline FcεRα nucleic acid molecule of the present invention can be isolated from its natural source or can be produced using recombinant DNA technology (e.g., polymerase chain reaction (PCR) amplification, cloning) or chemical synthesis. Isolated feline FcεRα nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode a feline FcεRα protein of the present invention or to form stable hybrids under stringent conditions with natural gene isolates.

A feline FcεRα nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification), synthesis of oligonucleotide mixtures and ligation of mixture groups to "build" a mixture of nucleic acid molecules and combinations thereof. Nucleic acid molecule homologs can be selected by hybridization with a feline FcεRα gene or by screening for function of a protein encoded by the nucleic acid molecule (e.g., ability of a feline FcεRα protein to bind IgE).

An isolated nucleic acid molecule of the present invention can include a nucleic acid sequence that encodes at least one feline FcεRα protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a feline FcεRα protein.

One embodiment of the present invention is a feline FcεRα nucleic acid molecule that hybridizes under stringent hybridization conditions with nucleic acid molecule nfelFc$_\epsilon$Rα$_{1069}$ and preferably with a nucleic acid molecule having nucleic acid sequence SEQ ID NO:1 and/or SEQ ID NO:3.

Comparison of nucleic acid sequence SEQ ID NO:1 (i.e., the nucleic acid sequence of the coding strand of nfelFc$_\epsilon$Rα$_{1069}$) with nucleic acid sequences reported in GenBank indicates that SEQ ID NO:1 showed the most homology, i.e., about 77% identity a canine Fc epsilon receptor alpha chain gene.

Preferred feline FcεRα nucleic acid molecules include nucleic acid molecules having a nucleic acid sequence that is at least about 80%, preferably at least about 85%, more preferably at least about 90%, and even more preferably at least about 95% identical to nucleic acid sequence SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and/or SEQ ID NO:16.

Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and/or SEQ ID NO:16, that is capable of hybridizing to a feline FcεRα gene of the present invention, as well as allelic variants thereof. A more preferred nucleic acid molecule includes the nucleic acid sequence SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and/or SEQ ID NO:16, as well as allelic variants of such a nucleic acid molecule. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include nfelFc$_\epsilon$Rα$_{1069}$, nfelFc$_\epsilon$Rα$_{789}$, nfelFc$_\epsilon$Rα$_{714}$, nfelFc$_\epsilon$Rα$_{597}$ and nfelFc$_\epsilon$Rα$_{522}$.

The present invention also includes a nucleic acid molecule encoding a protein having at least a portion of SEQ ID NO:2, SEQ ID NO:7, SEQ ID NO:12 and SEQ ID NO:13, including nucleic acid molecules that have been modified to accommodate codon usage properties of the cells in which such nucleic acid molecules are to be expressed.

Knowing the nucleic acid sequences of certain feline FcεRα nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain feline FcεRα nucleic acid molecules from other cats. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include feline basophil cell, mast cell, mastocytoma cell, dendritic cell, B lymphocyte, macrophage, eosinophil, and/or monocyte cDNA libraries as well as genomic DNA libraries. Similarly, preferred DNA sources to screen or from which to amplify nucleic acid molecules include feline basophil cells, mast cells, mastocytoma cells, dendritic cells, B lymphocytes, macrophages, eosinophils, and/or monocytes cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising feline FcεRα genes or other feline FcεRα nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit feline FcεRα protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of feline FcεRα nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with cats.

Suitable and preferred nucleic acid molecules to include in recombinant vectors of the present invention are as disclosed herein. Preferred nucleic acid molecules to include in recombinant vectors, and particularly in recombinant molecules, include nfelFcεRα$_{1069}$, nfelFcεRα$_{789}$, nfelFcεRα$_{714}$, nfelFcεRα$_{597}$ and nfelFcεRα$_{522}$. A particularly preferred recombinant molecule of the present invention includes pVL-nfelFcεRα$_{597}$, the production of which are described in the Examples section.

Recombinant molecules of the present invention may also (a) contain secretory signals (i.e., signal segment nucleic acid sequences) to enable an expressed feline FcεRα protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include feline FcεRα nucleic acid molecules disclosed herein. Particularly preferred nucleic acid molecules with which to transform a cell include nfelFc$_\epsilon$Rα$_{1069}$, nfelFc$_\epsilon$Rα$_{789}$, nfelFc$_\epsilon$Rα$_{714}$, nfelFc$_\epsilon$Rα$_{597}$ and nfelFc$_\epsilon$Rα$_{522}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing feline FcεRα proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_x$3987 and SR-11 $_x$4072; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. A particularly preferred recombinant molecule includes pVL-nfelFc$_\epsilon$Rα$_{597}$.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein. A particularly preferred recombinant cell includes *S. frugiperda*:pVL-nfelFc$_\epsilon$Rα$_{597}$. Details regarding the production of this recombinant cell is disclosed herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated feline FcεRα proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a feline FcεRα protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, rmicrotiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial.

The present invention also includes isolated (i.e., removed from their natural milieu) antibodies that selectively bind to a feline FcεRα protein of the present invention or a mimetope thereof (i.e., anti-feline FcεRα antibodies). As used herein, the term "selectively binds to" a feline FcεRα protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-feline FcεRα antibody preferably selectively binds to a feline FcεRα protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce feline FcεRα proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as tools to detect Fc epsilon receptor in the presence or absence of IgE and/or (b) as tools to screen expression libraries and/or to recover desired proteins of the present invention from a mixture of proteins and other contaminants. Furthermore, antibodies of the present invention can be used to target cytotoxic agents to cells having Fc epsilon receptors such as those disclosed herein in order to directly kill such cells. Targeting can be accomplished by conjugating (i.e., stably joining) such antibodies to the cytotoxic agents using techniques known to those skilled in the art. Suitable cytotoxic agents are known to those skilled in the art. Antibodies of the present invention, including FcεRα-binding portions thereof, can also be used, for example, to inhibit binding of IgE to Fc epsilon receptors, to produce anti-feline FcεRα idiotypic antibodies, to purify cells having feline FcεRα proteins, to stimulate intracellular signal transduction through a feline FcεRα and to identify cells having feline FcεRα proteins.

A feline FcεRα molecule of the present invention can include chimeric molecules comprising a portion of a feline FcεRα molecule that binds to an IgE and a second molecule that enables the chimeric molecule to be bound to a substrate in such a manner that the FcεRα molecule portion binds to IgE in essentially the same manner as a FcεRα molecule that is not bound to a substrate. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

A feline FcεRα molecule of the present invention can be contained in a formulation, herein referred to as a FcεRα molecule formulation. For example, a feline FcεRα molecule can be combined with a buffer in which the feline FcεRα molecule is solubilized, and/or with a carrier. Suitable buffers and carriers are known to those skilled in the art. Examples of suitable buffers include any buffer in which a feline FcεRα molecule can function to selectively bind to IgE, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be mixed with feline FcεRα molecules or conjugated (i.e., attached) to feline FcεRα molecules in such a manner as to not substantially interfere with the ability of the feline FcεRα molecules to selectively bind to IgE.

A feline FcεRα protein of the present invention can be bound to the surface of a cell comprising the feline FcεRα protein. A preferred feline FcεRα protein-bearing cell includes a recombinant cell comprising a nucleic acid molecule encoding a feline FcεRα protein of the present invention. A more preferred recombinant cell of the present invention comprises a nucleic acid molecule that encodes at least one of the following proteins: $PfelFc_{\epsilon}R\alpha_{238}$ and $PfelFc_{\epsilon}R\alpha_{263}$. An even more preferred recombinant cell comprises a nucleic acid molecule including $nfel Fc_{\epsilon}R\alpha_{1069}$, $nfelFc_{\epsilon}R\alpha_{789}$ and $nfelFc_{\epsilon}R\alpha_{714}$ with a recombinant cell comprising a nucleic acid molecule comprising a nucleic acid sequence including SEQ ID NO:1, SEQ ID NO:4 or SEQ ID NO:6, or a nucleic acid molecule comprising an allelic variant of a nucleic acid molecule comprising SEQ ID NO:1, SEQ ID NO:4 or SEQ ID NO:6, being even more preferred.

In addition, a feline FcεRα molecule formulation of the present invention can include not only a feline FcεRα molecule but also one or more additional antigens or antibodies useful in detecting IgE. As used herein, an antigen refers to any molecule capable of being selectively bound by an antibody. As used herein, selective binding of a first molecule to a second molecule refers to the ability of the first molecule to preferentially bind (e.g., having higher affinity higher avidity) to the second molecule when compared to the ability of a first molecule to bind to a third molecule. The first molecule need not necessarily be the natural ligand of the second molecule. Examples of such antibodies include, but are not limited to, antibodies that bind selectively to the constant region of an IgE heavy (i.e., anti-IgE isotype antibody) or antibodies that bind selectively to an IgE having a specific antigen specificity (i.e., anti-IgE idiotypic antibody). Suitable anti-IgE antibodies for use in a formulation of the present invention are not capable of cross-linking two or more IgE antibodies. Preferred anti-IgE antibodies include Fab fragments of the antibodies (as defined in Janeway et al., ibid.). Examples of such antigens include any antigen known to induce the production of IgE. Preferred antigens include allergens and parasite antigens. Allergens of the present invention are preferably derived from fungi, trees, weeds, shrubs, grasses, wheat, corn, soybeans, rice, eggs, milk, cheese, bovines (or cattle), poultry, swine, cats, sheep, yeast, fleas, flies, mosquitos, mites, midges, biting gnats, lice, bees, wasps, ants, true bugs or ticks. A suitable flea allergen includes an allergen derived from a flea, in particular flea saliva antigen. A preferred flea allergen includes a flea saliva antigen. Preferred flea saliva antigens include antigens such as those disclosed in PCT Patent Publication No. WO 96/11271, published Apr. 18, 1996, by Frank et al. (this publication is incorporated by reference herein in its entirety), with flea saliva products and flea saliva proteins being particularly preferred. According to the present invention, a flea saliva protein includes a protein produced by recombinant DNA methods, as well as proteins isolated by other methods disclosed in PCT Patent Publication No. WO 96/11271.

Preferred general allergens include those derived from grass, Meadow Fescue, curly dock, plantain, Mexican firebush, lamb's quarters, pigweed, ragweed, sage, elm, cocklebur, box elder, walnut, cottonwood, ash, birch, cedar, oak, mulberry, cockroach, Dermataphagoides, Alternaria, Aspergillus, Cladosporium, Fusarium, Helminthosporium, Mucor, Penicillium, Pullularia, Rhizopus and/or Tricophyton. More preferred general allergens include those derived from Johnson grass, Kentucky blue grass, meadow fescue, orchard grass, perennial rye grass, red top grass, timothy grass, Bermuda grass, brome grass, curly dock, English plantain, Mexican firebush, lamb's quarters, rough pigweed short ragweed, wormwood sage, American elm, common cocklebur, box elder, black walnut, eastern cottonwood, green ash, river birch, red cedar, red oak, red mulberry, cockroach, *Dermataphagoides farinae, Alternaria alternata, Aspergillus fumigatus, Cladosporium herbarum, Fusarium vasinfectum, Helminthosporium sativum, Mucor recemosus, Penicillium notatum, Pullularia pullulans, Rhizopus nigricans* and/or *Tricophyton spp*. Preferred parasite antigens include, but are not limited to, helminth antigens, in particular heartworm antigens, such as Di33 (described in U.S. patent application Ser. No. 08/715,628, filed Sep. 18, 1996, by Grieve et al., which is incorporated by reference herein in its entirety). The term "derived from" refers to a natural allergen of such plants or organisms (i.e., an allergen directly isolated from such plants or organisms), as well as, non-natural allergens of such plants or organisms that posses at least one epitope capable of eliciting an immune response against an allergen (e.g., produced using recombinant DNA technology or by chemical synthesis).

One embodiment of the present invention is a method to detect IgE which includes the steps of: (a) contacting an isolated feline FcεRα molecule with a putative IgE-containing composition under conditions suitable for formation of a feline FcεRα molecule:IgE complex; and (b) detecting the presence of IgE by detecting the feline FcεRα molecule:IgE complex. Presence of such a feline FcεRα molecule:IgE complex indicates that the animal is producing IgE. Preferred IgE to detect using a feline FcεRα molecule include feline IgE, canine IgE, equine IgE and human IgE, with feline IgE being particularly preferred. The present method can further include the step of determining whether an IgE complexed with a feline FcεRα protein is heat labile. Preferably, a heat labile IgE is determined by incubating an IgE at about 56° C. for about 3 or about 4 hours. Without being bound by theory, the inventors believe that heat labile forms of IgE bind to certain allergens and non-heat labile forms of IgE bind to other types of allergens. As such, detection of heat labile IgE compared with non-heat labile IgE can be used to discriminate between allergen sensitivities. For example, the inventors believe that IgE antibodies that bind to certain flea allergens and heartworm allergens are heat labile while IgE antibodies that bind to certain plant allergens are not heat labile. Thus, the presence of non-heat labile IgE may indicate that an animal is sensitive to certain plant allergens but not to certain flea or heartworm allergens. Moreover, the inventors believe that identification of heat labile IgE and non-heat labile IgE using a feline FcεRα protein suggests the presence of different sub-populations of IgE that may or may not have substantially similar structures to known IgE antibodies. As such, a feline FcεRα protein of the present invention may be useful for detecting molecules bound by the feline FcεRα protein but not identical to a known IgE.

As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, equine refers to any member of the horse family, including horses, donkeys, mules and zebras.

As used herein, the term "contacting" refers to combining or mixing, in this case a putative IgE-containing composition with a feline FcεRα molecule. Formation of a complex between a feline FcεRα molecule and an IgE refers to the ability of the feline FcεRα molecule to selectively bind to the IgE in order to form a stable complex that can be measured (i.e., detected). As used herein, the term selectively binds to an IgE refers to the ability of a feline FcεRα molecule of the present invention to preferentially bind to IgE, without being able to substantially bind to other antibody isotypes. Binding between a feline FcεRα molecule and an IgE is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., ibid.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between feline FcεRα molecule and any IgE in the composition can be measured (i.e., detected, determined) using a variety of methods standard in the art (see, for example, Sambrook et al. ibid.), examples of which are disclosed herein.

In one embodiment, a putative IgE-containing composition of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces. Such a composition of the present method can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

In another embodiment, a IgE-containing composition of the present method includes a cell that produces IgE. Such a cell can have IgE bound to the surface of the cell and/or can secrete IgE. An example of such a cell includes myeloma cells. IgE can be bound to the surface of a cell either directly to the membrane of the cell or bound to a molecule (e.g., an antigen) bound to the surface of the cell.

A complex can be detected in a variety of ways including, but not limited to use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a Bio-Core™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker to the feline FcεRα molecule or to a reagent that selectively binds to the feline FcεRα molecule or to the IgE being detected (described in more detail below) aids in detecting complex formation. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.). According to the present invention, a detectable marker can be connected to a feline FcεRα molecule using, for example, chemical conjugation or recombinant DNA technology (e.g., connection of a fusion segment such as that described herein for a metal binding domain; an immunoglobulin binding; a sugar binding domain; and a "tag" domain). Preferably a carbohydrate group of the feline FcεRα molecule is chemically conjugated to biotin.

In one embodiment, a complex is detected by contacting a putative IgE-containing composition with a feline FcεRα molecule that is conjugated to a detectable marker. A suitable detectable marker to conjugate to a feline FcεRα molecule includes, but is not limited to, a radioactive label, a fluorescent label, an enzyme label, a chemiluminescent label, a chromophoric label or a ligand. A detectable marker is conjugated to a feline FcεRα molecule in such a manner as not to block the ability of the feline FcεRα molecule to bind to the IgE being detected. Preferably, a carbohydrate group of a feline FcεRα molecule is conjugated to biotin.

In another embodiment, a feline FcεRα molecule:IgE complex is detected by contacting a putative IgE-containing composition with a feline FcεRα molecule and then contacting the complex with an indicator molecule. Suitable indicator molecules of the present invention include molecules that can bind to either the feline FcεRα molecule or to the IgE antibody. As such, an indicator molecule can comprise, for example, an antigen, an antibody and a lectin, depending upon which portion of the feline FcεRα molecule:IgE complex is being detected. Preferred indicator molecules that are antibodies include, for example, anti-IgE antibodies and anti-feline FcεRα antibodies. Preferred lectins include those lectins that bind to high-mannose groups. More preferred lectins bind to high-mannose groups present on a feline FcεRα protein of the present invention produced in insect cells. An indicator molecule itself can be attached to a detectable marker of the present invention. For example, an antibody can be conjugated to biotin, horseradish peroxidase, alkaline phosphatase or fluorescein.

In one preferred embodiment, a feline FcεRα molecule:IgE complex is detected by contacting the complex with an indicator molecule that selectively binds to a feline FcεRα molecule of the present invention. Examples of such indicator molecule includes, but are not limited to, an antibody that selectively binds to a feline FcεRα molecule (referred to herein as an anti-feline FcεRα antibody) or a compound that selectively binds to a detectable marker conjugated to a feline FcεRα molecule. A feline FcεRα molecule conjugated to biotin is preferably detected using streptavidin, more preferably using ImmunoPure® NeutrAvidin (available from Pierce, Rockford, Ill.).

In another preferred embodiment, a feline FcεRα molecule:IgE complex is detected by contacting the complex with indicator molecule that selectively binds to an IgE antibody (referred to herein as an anti-IgE reagent). Examples of such an anti-IgE antibody include, but are not limited to, a secondary antibody that is an anti-isotype antibody (e.g., an antibody that selectively binds to the constant region of an IgE), an antibody-binding bacterial surface protein (e.g., Protein A or Protein G), an antibody-binding cell (e.g., a B cell, a T cell, a natural killer cell, a polymorphonuclear leukocyte cell, a monocyte cell or a macrophage cell), an antibody-binding eukaryotic cell surface protein (e.g., a Fc receptor), and an antibody-binding complement protein. A preferred indicator molecule includes an anti-feline IgE antibody. As used herein, an anti-IgE antibody includes not only a complete antibody but also any subunit or portion thereof that is capable of selectively binding to an IgE heavy chain constant region. For example, an anti-IgE reagent can include an Fab fragment or a F(ab')$_2$ fragment, both of which are described in detail in Janeway et al., in *Immunobiology, the Immune System in Health and Disease*, Garland Publishing, Inc., N.Y., 1996 (which is incorporated herein by this reference in its entirety).

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect IgE is an immunosorbent assay. An immunoabsorbent assay of the present invention comprises a capture molecule and an indicator molecule. A capture molecule of the present invention binds to an IgE in such a manner that the IgE is immobilized to a substrate. As such, a capture molecule is preferably immobilized to a substrate of the present invention prior to exposure of the capture molecule to a putative IgE-containing composition. An indicator molecule of the present invention detects the presence of an IgE bound to a capture molecule. As such, an indicator molecule preferably is not immobilized to the same substrate as a capture molecule prior to exposure of the capture molecule to a putative IgE-containing composition.

A preferred immunoabsorbent assay method includes a step of either: (a) immobilizing a feline FcεRα molecule on a substrate prior to contacting a feline FcεRα molecule with a putative IgE-containing composition to form a feline FcεRα molecule-immobilized substrate; and (b) binding a putative IgE-containing composition on a substrate prior to contacting a feline FcεRα molecule with a putative IgE-containing composition to form a putative IgE-containing composition-bound substrate. Preferably, the substrate includes a non-coated substrate, a feline FcεRα molecule-immobilized substrate, an antigen-immobilized substrate or an anti-IgE antibody-immobilized substrate.

Both a capture molecule and an indicator molecule of the present invention are capable of binding to an IgE. Preferably, a capture molecule binds to a different region of an IgE than an indicator molecule, thereby allowing a capture molecule to be bound to an IgE at the same time as an indicator molecule. The use of a reagent as a capture molecule or an indicator molecule depends upon whether the molecule is immobilized to a substrate when the molecule is exposed to an IgE. For example, a feline FcεRα molecule of the present invention is used as a capture molecule when the feline FcεRα molecule is bound on a substrate. Alternatively, a feline FcεRα molecule is used as an indicator molecule when the feline FcεRα molecule is not bound on a substrate. Suitable molecules for use as capture molecules or indicator molecules include, but are not limited to, a feline FcεRα molecule of the present invention, an antigen reagent or an anti-IgE antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgE idiotypic antibody and an anti-IgE isotypic antibody. Preferred tertiary molecules can be selected by a skilled artisan based upon the characteristics of the secondary molecule. The same strategy is applied for subsequent layers.

In one embodiment, a specific antigen is used as a capture molecule by being immobilized on a substrate, such as a microtiter dish well or a dipstick. Preferred antigens include those disclosed herein. A biological sample collected from an animal is applied to the substrate and incubated under conditions suitable (i.e., sufficient) to allow for antigen:IgE complex formation bound to the substrate (i.e., IgE in a sample binds to an antigen immobilized on a substrate). Excess non-bound material (i.e., material from the biological sample that has not bound to the antigen), if any, is removed from the substrate under conditions that retain antigen:IgE complex binding to the substrate. Preferred conditions are generally disclosed in Sambrook et al., ibid. An indicator molecule that can selectively bind to an IgE bound to the antigen is added to the substrate and incubated to allow formation of a complex between the indicator molecule and the antigen:IgE complex. Excess indicator molecule is removed, a developing agent is added if required, and the substrate is submitted to a detection device for analysis. A preferred indicator molecule for this embodiment is a feline FcεRα molecule, preferably conjugated to biotin, to a fluorescent label or to an enzyme label.

In one embodiment, a feline FcεRα molecule is used as a capture molecule by being immobilized on a substrate, such as a microtiter dish well or a dipstick. A biological sample collected from an animal is applied to the substrate and incubated under conditions suitable to allow for feline FcεRα molecule:IgE complex formation bound to the substrate. Excess non-bound material, if any, is removed from the substrate under conditions that retain feline FcεRα molecule:IgE complex binding to the substrate. An indicator molecule that can selectively bind to an IgE bound to the feline FcεRα molecule is added to the substrate and incubated to allow formation of a complex between the indicator molecule and the feline FcεRα molecule:IgE complex. Preferably, the indicator molecule is conjugated to a detectable marker (preferably to an enzyme label, to a colorimetric label, to a fluorescent label, to a radioisotope, or to a ligand such as of the biotin or avidin family). Excess indicator molecule is removed, a developing agent is added if required, and the substrate is submitted to a detection device for analysis. A preferred indicator molecule for this embodiment is an antigen that will bind to IgE in the biological sample or an anti-IgE isotype or idiotype antibody, either preferably being conjugated to fluorescein or biotin.

In one embodiment, an anti-IgE antibody (e.g., isotype or idiotype specific antibody) is used as a capture molecule by being immobilized on a substrate, such as a microtiter dish well or a dipstick. A biological sample collected from an animal is applied to the substrate and incubated under conditions suitable to allow for anti-IgE antibody:IgE complex formation bound to the substrate. Excess non-bound material, if any, is removed from the substrate under conditions that retain anti-IgE antibody:IgE complex binding to the substrate. A feline FcεRα molecule is added to the substrate and incubated to allow formation of a complex between the feline FcεRα molecule and the anti-IgE antibody:IgE complex. Preferably, the feline FcεRα molecule is conjugated to a detectable marker (preferably to biotin, an enzyme label or a fluorescent label). Excess feline FcεRα molecule is removed, a developing agent is added if required, and the substrate is submitted to a detection device for analysis.

In one embodiment, an immunosorbent assay of the present invention does not utilize a capture molecule. In this embodiment, a biological sample collected from an animal is applied to a substrate, such as a microtiter dish well or a dipstick, and incubated under conditions suitable to allow for IgE binding to the substrate. Any IgE present in the bodily fluid is immobilized on the substrate. Excess non-bound material, if any, is removed from the substrate under conditions that retain IgE binding to the substrate. A feline FcεRα molecule is added to the substrate and incubated to allow formation of a complex between the feline FcεRα molecule and the IgE. Preferably, the feline FcεRα molecule is conjugated to a detectable marker (preferably to biotin, an enzyme label or a fluorescent label). Excess feline FcεRα molecule is removed, a developing agent is added if required, and the substrate is submitted to a detection device for analysis.

Another preferred method to detect IgE is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a bead conjugated to an antigen, the labeling reagent being impregnated within the support structure in a labeling zone; and (c) a capture reagent comprising an IgE-binding composition. Preferred antigens include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the labeling reagent that binds to IgE. A preferred labeling reagent is an antigen conjugated, either directly or through a linker, to a plastic bead substrate, such as to a latex bead. The substrate also includes a detectable marker, preferably a calorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case a feline FcεRα molecule, as disclosed above, that immobilizes the IgE complexed to the antigen in the capture zone. The capture reagent is preferably fixed to the support structure by drying or lyophilizing. The labeling reagent accumulates in the capture zone and the accumulation is assessed visually or by an optical detection device.

In another embodiment, a lateral flow apparatus used to detect IgE includes: (a) a support structure defining a flow path; (b) a labeling reagent comprising a feline FcεRα molecule as described above, the labeling reagent impregnated within the support structure in a labeling zone; and (c) a capture reagent comprising an antigen, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

One embodiment of the present invention is an inhibition assay in which the presence of IgE in a putative IgE-containing composition is determined by adding such composition to a feline FcεRα molecule of the present invention and an isolated IgE known to bind to the feline FcεRα molecule. The absence of binding of the feline FcεRα molecule to the known IgE indicates the presence of IgE in the putative IgE-containing composition. The known IgE is preferably conjugated to a detectable marker.

The present invention also includes kits to detect IgE based on each of the disclosed detection methods. One embodiment is a kit to detect IgE comprising a feline FcεRα protein and a means for detecting an IgE. Suitable and preferred feline FcεRα protein are disclosed herein. Suitable means of detection include compounds disclosed herein that bind to either the feline FcεRα protein or to an IgE. A preferred kit of the present invention further comprises a detection means including one or more antigens disclosed herein, an antibody capable of selectively binding to an IgE disclosed herein and/or a compound capable of binding to a detectable marker conjugated to a feline FcεRα protein (e.g., avidin, streptavidin and ImmunoPure® NeutrAvidin when the detectable marker is biotin). Such antigens preferably induce IgE antibody production in animals including canines, felines and/or equines.

A preferred embodiment of a kit of the present invention is a flea allergen kit comprising a flea allergen such as those disclosed herein. A particularly preferred flea allergen for use with a flea allergen kit includes a flea saliva product and/or an isolated flea saliva protein.

Another preferred kit of the present invention is a general allergen kit comprising an allergen common to all regions of the United States and a feline FcεRα protein of the present invention. As used herein, a "general allergen" kit refers to a kit comprising allergens that are found substantially throughout the United States (i.e., essentially not limited to certain regions of the United States). A general allergen kit provides an advantage over regional allergen kits because a single kit can be used to test an animal located in most geographical locations on the United States. Suitable and preferred general allergens for use with a general allergen kit of the present invention include those general allergens disclosed herein.

Another preferred kit of the present invention is a food allergen kit comprising a food allergen including beef, chicken, pork, a mixture of fish, such as cod, halibut or and tuna, egg, milk, Brewer's yeast, whole wheat, corn, soybean, cheese and rice, and a feline FcεRα molecule of the present invention. Preferably, the beef, chicken, pork, fish, corn and rice, are cooked.

A preferred kit of the present invention includes those in which the allergen is immobilized on a substrate. If a kit comprises two or more antigens, the kit can comprise one or more compositions, each composition comprising one antigen. As such, each antigen can be tested separately. A kit can also contain two or more diagnostic reagents for IgE, additional isolated IgE antigens and/or antibodies as disclosed herein. Particularly preferred are kits used in a lateral flow assay format. It is within the scope of the present invention that a lateral flow assay kit can include one or more lateral flow assay apparatuses. Multiple lateral flow apparatuses can be attached to each other at one end of each apparatus, thereby creating a fan-like structure.

In particular, a method and kit of the present invention are useful for diagnosing abnormal conditions in animals that are associated with changing levels of IgE. Particularly preferred conditions to diagnose include allergies, parasitic infections and neoplasia. For example, a method and kit of the present invention are particularly useful for detecting flea allergy dermatitis (FAD), when such method or kit includes the use of a flea saliva antigen. FAD is defined as a hypersensitive response to fleabites. Preferably, a putative IgE-containing composition is obtained from an animal suspected of having FAD. Preferred animals include those disclosed herein, with dogs and cats being more preferred. In addition, methods and kits of the present invention are particularly useful for detecting helminth infection, in particular heartworm infection, when such methods or kits include the use of a helminth antigen, such as Di33. Preferably, a putative IgE-containing composition is obtained from an animal suspected of having a helminth infection. Preferred animals include those disclosed herein, with dogs and cats being more preferred.

One embodiment of the present invention is a therapeutic composition that, when administered to an animal in an effective manner, is capable of reducing Fc receptor mediated reactions associated with diseases related to biological responses involving Fc receptor function. A therapeutic composition of the present invention can include: an isolated feline FcεRα protein, or homolog thereof; a mimetope of a feline FcεRα protein; an isolated nucleic acid molecule that hybridizes under stringent hybridization conditions with a feline FcεRα gene; an isolated antibody that selectively binds to a feline FcεRα protein; and/or an inhibitor that interferes with formation of a complex between a feline FcεRα protein and IgE.

One embodiment of a therapeutic composition of the present invention is a therapeutic compound comprising a feline FcεRα molecule of the present invention, that binds to an IgE. According to the present invention, a feline FcεRα molecule competes for IgE with naturally-occurring Fc epsilon receptors, particularly those on mastocytoma cells, mast cells or basophils, so that IgE is bound to the administered feline FcεRα molecule and thus is unable to bind to Fc epsilon receptor on a cell, thereby inhibiting mediation of a biological response. Preferred feline FcεRα molecule for use in a therapeutic composition comprises a feline FcεRα protein, or homolog thereof, as described herein, particularly a fragment thereof, which binds to IgE. Feline FcεRα molecules for use in a therapeutic composition can be in a monovalent and/or multivalent form, so long as the feline FcεRα molecule is capable of binding to IgE. A more preferred feline FcεRα molecule for use in a therapeutic composition includes a soluble fragment of a feline FcεRα protein. A preferred feline FcεRα protein is encoded by nfelFc$_ε$Rα$_{522}$ and an even more preferred feline FcεRα protein is PfelFc$_ε$Rα$_{174}$.

Examples of suitable nucleic acid molecules for use in a therapeutic composition of the present invention are disclosed herein.

Another embodiment of a therapeutic composition of the present invention comprises a therapeutic compound that interferes with the formation of a complex between feline FcεRα protein and IgE, usually by binding to or otherwise interacting with or otherwise modifying the feline FcεRα protein's IgE binding site. Feline FcεRα protein inhibitors can also interact with other regions of the feline FcεRα protein to inhibit feline FcεRα protein activity, for example, by allosteric interaction. An inhibitor of a feline FcεRα protein can interfere with FcεRα protein and IgE complex formation by, for example, preventing formation of a FcεRα protein and IgE complex or disrupting an existing FcεRα protein and IgE complex causing the FcεRα protein and IgE to dissociate. An inhibitor of a feline FcεRα protein is usually a relatively small. Preferably, a feline FcεRα protein inhibitor of the present invention is identified by its ability to bind to, or otherwise interact with, a feline FcεRα protein, thereby interfering with the formation of a complex between a feline FcεRα protein and IgE.

Preferred inhibitors of a feline FcεRα protein of the present invention include, but are not limited to, a substrate analog of a feline FcεRα protein, a mimetope of a feline FcεRα protein, a soluble (i.e., secreted form of a feline FcεRα protein) portion of a feline FcεRα protein that binds to IgE, and other molecules that bind to a feline FcεRα protein (e.g., to an allosteric site) in such a manner that IgE-binding activity of the feline FcεRα protein is inhibited. A feline FcεRα protein substrate analog refers to a compound that interacts with (e.g., binds to, associates with, modifies) the IgE-binding site of a feline FcεRα protein. A preferred feline FcεRα protein substrate analog inhibits IgE-binding activity of a feline FcεRα protein. Feline FcεRα protein substrate analogs can be of any inorganic or organic composition, and, as such, can be, but are not limited to, peptides, nucleic acids, and peptidomimetic compounds. Feline FcεRα protein substrate analogs can be, but need not be, structurally similar to a feline FcεRα protein's natural substrate (e.g., IgE) as long as they can interact with the active site (e.g., IgE-binding site of that feline FcεRα). Feline FcεRα protein substrate analogs can be designed using computer-generated structures of feline FcεRα proteins of the present invention or computer structures of, for example, the Fc domain of IgE. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a feline FcεRα protein or anti-feline FcεRα idiotypic antibody). A preferred feline FcεRα protein substrate analog is a peptidomimetic compound (i.e., a compound that is structurally and/or functionally similar to a natural substrate of a feline FcεRα protein of the present invention, particularly to the region of the substrate that binds to a feline FcεRα protein, but that inhibits IgE binding upon interacting with the IgE binding site).

Feline FcεRα molecules, as well as other inhibitors and therapeutic compounds, can be used directly as compounds in compositions of the present invention to treat animals as long as such compounds are not harmful to the animals being treated.

The present invention also includes a therapeutic composition comprising one or more therapeutic compounds of the present invention. Examples of such therapeutic compounds are disclosed herein.

In one embodiment, a therapeutic composition of the present invention can be used to reduce a Fc epsilon receptor-mediated biological response in an animal by administering such a composition to an animal. Preferably, an animal is treated by administering to the animal a therapeutic composition of the present invention in such a manner that a therapeutic compound (e.g., an inhibitor of a feline FcεRα protein, an anti-feline FcεRα antibody, an inhibitor of IgE, or nucleic acid molecules encoding feline FcεRα proteins) binds to an IgE or a Fc epsilon receptor in the animal. Such administration could be by a variety of routes known to those skilled in the art including, but not limited to, subcutaneous, intradermal, intravenous, intranasal, oral, transdermal, intramuscular routes and other parenteral routes.

Compositions of the present invention can be administered to any animal having a Fc epsilon receptor or an IgE that binds to a therapeutic compound of the present invention or to a protein expressed by a nucleic acid molecule contained in a therapeutic composition. Preferred animals to treat include mammals and birds, with cats, dogs, horses, humans and other pets, work and/or economic food animals. Particularly preferred animals to protect are cats and dogs.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, — or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL4), interleukin 5 (IL-5), interleukin 6 (IL-6) interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to reduce Fc epsilon receptor-mediated biological responses in the animal. As used herein, a Fc epsilon receptor-mediated biological response refers to cellular responses that occur when Fc epsilon receptor is complexed with IgE. For example, a Fc epsilon receptor-mediated biological response includes release of biological mediators, such as histamine, prostaglandins and/or proteases, that can trigger clinical symptoms of allergy. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting (i.e., preventing or treating) an animal from disease when administered one or more times over a suitable time period. The need for additional administrations of a therapeutic composition can be determined by one of skill in the art in accordance with the given condition of a patient. For example, to regulate an antigen-specific Fc epsilon receptor-mediated response, a therapeutic composition may be administered more frequently when an antigen is present in a patient's environment in high amounts and less frequently when the antigen is present in lower amounts.

According to one embodiment, a nucleic acid molecule of the present invention can be administered to an animal in a fashion to enable expression of that nucleic acid molecule into a feline FcεRα protein or a feline FcεRα RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, *Science* 247, 1465–1468) or (b) administering a nucleic acid molecule packaged as a recombinant virus or as a recombinant cell (i.e., the nucleic acid molecule is delivered by a viral or cellular vehicle).

A naked nucleic acid molecule of the present invention includes a nucleic acid molecule of the present invention and preferably includes a recombinant molecule of the present invention that preferably is replication, or otherwise amplification, competent. A naked nucleic acid of the present invention can comprise one or more nucleic acid molecules of the present invention in the form of, for example, a bicistronic recombinant molecule having, for example one or more internal ribosome entry sites. Preferred naked nucleic acid molecules include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

A recombinant virus of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, picornaviruses and retroviruses. Preferred recombinant viruses are those based on alphaviruses (such as Sindbis virus), raccoon poxviruses, species-specific herpesviruses and species-specific poxviruses. An example of methods to produce and use alphavirus recombinant virus is disclosed in PCT Publication No. WO 94/17813, by Xiong et al., published Aug. 18, 1994, which is incorporated by reference herein in its entirety.

When administered to an animal, a recombinant virus of the present invention infects cells within the recipient animal and directs the production of a protein or RNA nucleic acid molecule that is capable of reducing Fc epsilon receptor-mediated biological responses in the animal. For example, a recombinant virus comprising a feline FcεRα nucleic acid molecule of the present invention is administered according to a protocol that results in the animal producing an amount of protein or RNA sufficient to reduce Fc epsilon receptor-mediated biological responses. A preferred single dose of a recombinant virus of the present invention is from about $1 \times 10^4$ to about $1 \times 10^7$ virus plaque forming units (pfu) per kilogram body weight of the animal. Administration protocols are similar to those described herein for protein-based compositions, with subcutaneous, intramuscular, intranasal and oral administration routes being preferred.

A recombinant cell useful in a therapeutic composition of the present invention includes recombinant cells of the present invention that comprises at least one feline FcεRα of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. A recombinant cell of the present invention can be administered in a variety of ways but have the advantage that they can be administered orally, preferably at doses ranging from about $10^8$ to about $10^{12}$ cells per kilogram body weight. Administration protocols are similar to those described herein for protein compositions. Recombinant cells can comprise whole cells, cells stripped of cell walls or cell lysates.

One embodiment of the present invention is a method of immunotherapy comprising the steps of: (a) administering to an animal an effective amount of a therapeutic composition selected from the group consisting of an inhibitor of a feline FcεRα and a feline FcεRα protein (including homologs), wherein said feline FcεRα is capable of binding to IgE. Suitable therapeutic compositions and methods of administration methods are disclosed herein. According to the present invention, a therapeutic composition and method of the present invention can be used to prevent or alleviate symptoms associated with Fc epsilon receptor-mediated biological responses.

The efficacy of a therapeutic composition of the present invention to effect Fc epsilon receptor-mediated biological responses can be tested using standard methods for detecting Fc receptor-mediated immunity including, but not limited to, immediate hypersensitivity, delayed hypersensitivity, antibody-dependent cellular cytotoxicity (ADCC), immune complex activity, mitogenic activity, histamine release assays and other methods such as those described in Janeway et al., ibid.

An inhibitor of feline FcεRα activity can be identified using feline FcεRα proteins of the present invention by determining the ability of an inhibitor to prevent or disrupt complex formation between a feline FcεRα protein and IgE. One embodiment of the present invention is a method to identify a compound capable of inhibiting feline FcεRα activity. Such a method includes the steps of (a) contacting (e.g., combining, mixing) an isolated feline FcεRα protein with a putative inhibitory compound under conditions in which, in the absence of the compound, the feline FcεRα protein has IgE binding activity, and (b) determining if the putative inhibitory compound inhibits the IgE binding activity. Putative inhibitory compounds to screen include small organic molecules, antibodies (including mimetopes thereof) and substrate analogs. Methods to determine IgE binding activity are known to those skilled in the art.

The present invention also includes a test kit to identify a compound capable of inhibiting feline FcεRα activity. Such a test kit includes: an isolated feline FcεRα protein having IgE binding activity or a complex of feline FcεRα protein and IgE; and a means for determining the extent of inhibition of IgE binding activity in the presence of (i.e., effected by) a putative inhibitory compound Such compounds are also screened to identify those that are substantially not toxic in animals.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., ibid., and related references.

Example 1

This example describes the isolation, by DNA hybridization, of a nucleic acid molecule encoding a feline Fc epsilon receptor alpha chain (FcεRα) protein from *Felis domesticus*.

A feline FcεRα nucleic acid molecule was isolated from a feline (*Felis domesticus*) mastocytoma cDNA library by hybridizing the library with a mixture of $^{32}$P-labeled cDNA molecules encoding human and canine Fc epsilon receptor alpha chains, respectively. A feline mastocytoma cDNA library was prepared as follows. Total RNA was extracted from approximately 1.5 grams of tissue from a freshly harvested feline mastocytoma, using an acid-guanidinium-phenol-chloroform method similar to that described by Chomzynski et al., 1987, *Anal. Biochem.* 162,156–159. Poly A$^+$ selected RNA was separated from the total RNA preparation by oligo-dT cellulose chromatography using the mRNA Purification Kit (available from Pharmacia Biotech, Newark, N.J.; according to the method recommended by the manufacturer). A feline mastocytoma cDNA library was constructed in lambda-Uni-ZAP™ XR vector (available from Stratagene Cloning Systems, La Jolla, Calif.), using Stratagene's ZAP-cDNA Synthesis Kit protocol. Approximately 5 μg of feline mastocytoma Poly A$^+$ RNA was used to produce the feline mastocytoma cDNA library. Using a modification of the protocol described in the cDNA Synthesis Kit, the feline mastocytoma cDNA library was screened, using duplicate plaque lifts, with a mixture of $^{32}$P-labeled cDNAs encoding the human Fc epsilon receptor alpha chain (Kochan et al., *Nucleic Acids Res.*, 16:3584, 1988) and the canine Fc epsilon receptor alpha chain (Hayashi et al., GenBank accession number D 16413, 1993), repsectively. A plaque purified clone identified using the above screening method was converted into a double stranded recombinant molecule, herein denoted as nfelFc$_ε$Rα$_{1069}$, using ExAssist™ helper phage and SOLR™ *E. coli* according to the in vivo excision protocol described in the ZAP-cDNA Synthesis Kit (available from Stratagene). Double-stranded plasmid DNA was prepared using an alkaline lysis protocol, such as that described in Sambrook et al., ibid.

Example 2

This example describes the sequencing of plasmid DNA containing nfelFc$_ε$Rα$_{1069}$. Plasmid DNA containing nfelFc$_ε$Rα$_{1069}$ was sequenced by the Sanger dideoxy chain termination method, using the PRISM™ Ready Dye Terminator Cycle Sequencing Kit with Ampli Taq DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following their standard protocol. Samples were resuspended according to ABI protocols and were run on a Perkin-Elmer ABI PRISM™ 377 Automated DNA Sequencer. DNA sequence analysis, including the compilation of sequences and the determination of open reading frames, were performed using the MacVector™ program (available from the Eastman Kodak Company, New Haven, Conn.), or the DNAsis™ program (available from Hitachi Software, San Bruno, Calif.). Protein sequence analysis, including the determination of molecular weight and isoelectric point (pI) was performed using the MacVector™ program. An about 1069 nucleotide consensus sequence of the entire nfelFc$_ε$Rα$_{1069}$ DNA was determined; the sequences of the two complementary strands are presented as SEQ ID NO:1 (the coding strand) and SEQ ID NO:3 (the complementary strand). The nfelFc$_ε$Rα$_{1069}$ sequence contains a full length coding region. The apparent initiation (start) codon span from about nucleotide 65 to about nucleotide 67 and the apparent termination (stop) codon spans from about nucleotide 854 to about nucleotide 856, respectively, of SEQ ID NO:1. A putative polyadenylation signal (5' AATAAA 3') is located in a region spanning from about nucleotide 1032 to about nucleotide 1037 of SEQ ID NO:1. Translation of SEQ ID NO:1 yields a protein of about 263 amino acids, denoted PfelFc$_ε$Rα$_{263}$, the amino acid sequence of which is presented in SEQ ID NO:2. The nucleic acid molecule consisting of the coding region encoding PfelFc$_ε$Rα$_{263}$ is referred to herein as nfelFc$_ε$Rα$_{789}$, the nucleic acid sequence of which is represented in SEQ ID NO:4 (the coding strand) and SEQ ID NO:5 (the complementary strand). The amino acid sequence of PfelFc$_ε$Rα$_{263}$ (i.e., SEQ ID NO:2) predicts that PfelFc$_ε$Rα$_{263}$ has an estimated molecular weight of about 30.2 ID and an estimated pI of about 9.51. Analysis of SEQ ID NO:2 suggests the presence of a signal peptide encoded by a stretch of amino acids spanning from about amino acid 1 through about amino acid 25. The proposed mature protein, denoted herein as PfelFc$_ε$Rα$_{238}$, contains about 238 amino acids which is represented herein as SEQ ID NO:7. The amino acid sequence of PfelFc$_ε$Rα$_{238}$ (i.e., SEQ ID NO:7) predicts that PfelFc$_ε$Rα$_{238}$ has an estimated molecular weight of about 27.5 kD, an estimated pI of about 9.59 and five predicted asparagine-linked glycosylation sites extending from about amino acids 30–32, 36–38, 43–45, 136–138 and 141–143 respectively.

Homology searches of the non-redundant protein and nucleotide sequence databases were performed through the National Center for Biotechnology Information using the BLAST network. The protein database includes SwissProt+PIR+SPUpdate+Genpept+GPUpdate. The nucleotide database includes GenBank+EMBL+DDBJ+PDB. The highest scoring match of the homology search at the amino acid level was GenBank accession number J03605: *Homo Sapiens*, which was about 54% identical with SEQ ID NO:2. At the nucleotide level, the search was performed using SEQ ID NO:1, which was most similar to GenBank accession number D 16413, canine (i.e., dog) mRNA for immunoglobulin E receptor alpha chain, there being about 77% identity between feline and canine sequences.

Example 3

This Example demonstrates the production of secreted feline FcεRα chain protein in eukaryotic cells.

To produce a secreted form of the extracellular domain of the feline FcεRα chain, the hydrophobic transmembrane domain and the cytoplasmic tail of the feline FcεRα chain encoded by nfelFc$_\epsilon$Rα$_{1069}$ were removed as follows. A feline FcεRα chain extracellular domain nucleic acid molecule-containing a fragment of about 597 nucleotides was PCR amplified from nfelFc$_\epsilon$Rα$_{1069}$ using a sense primer felIgEr FWD having the nucleic acid sequence 5° CGC GAA TTC TATAAA TAT GCC GGT TTT CCT GGG AGG CCCTGC 3' (SEQ ID NO:9; EcoRI site shown in bold) and an antisense primer felIgEr REV having the nucleic acid sequence 5' GCG AGA TCT TTA GGA ATC TTT TCT CAC AAC GAT GTT GAG G 3' (SEQ ID NO:10; BglII site shown in bold). The resulting PCR product (referred to as Bv-nfelFc$_\epsilon$Rα$_{597}$) was digested with EcoRI and BglII and subcloned into unique with EcoRI and BglII sites of pVL1392 baculovirus shuttle plasmid (available from Pharmingen, San Diego, Calif.) to produce the recombinant molecule referred to herein as pVL-nfelFc$_\epsilon$Rα$_{597}$. Nucleic acid molecule Bv-nfelFc$_\epsilon$Rα$_{597}$ contained an about 597 nucleotide fragment encoding the extracellular domain of the feline FcεRα chain, extending from about nucleotide 65 through about 661 of SEQ ID NO:1, denoted herein as nucleic acid molecule nfelFc$_\epsilon$Rα$_{597}$, the coding strand of which has a nucleic acid sequence denoted SEQ ID NO:11. Translation of SEQ ID NO:11 indicates that nucleic acid molecule nfelF$_\epsilon$Rα$_{597}$ encodes a FcεRα protein of about 199 amino acids, referred to herein as PfelFc$_\epsilon$Rα$_{199}$, having amino acid sequence SEQ ID NO:12. Nucleic acid molecule nfelFc$_\epsilon$Rα$_{597}$ encodes a secretable form of the feline FcεRα chain. The processed protein product encoded by nfelFc$_\epsilon$Rα$_{597}$ is about 174 amino acids and does not possess a leader sequence or a transmembrane domain. Such processed protein is denoted herein as PfelFc$_\epsilon$Rα$_{174}$ having amino acid sequence SEQ ID NO:13. The coding region for PfelFc$_\epsilon$Rα$_{174}$ is denoted nfelFc$_\epsilon$Rα$_{522}$, the coding strand of which has a nucleic acid sequence denoted SEQ ID NO:14. The complement of SEQ ID NO:14 is represented herein by SEQ ID NO:15.

The resultant recombinant molecule, pVL-nfelFc$_\epsilon$Rα$_{597}$, was verified for proper insert orientation by restriction mapping. Such a recombinant molecule was co-transfected with a linear Baculogold baculovirus DNA (available from Pharmingen) into *S. frugiperda* Sf9 cells (available from InVitrogen) to form a recombinant cell denoted *S. frugiperda*:pVL-nfelFc$_\epsilon$Rα$_{597}$. *S. frugiperda*:pVL-nfelFc$_\epsilon$Rα$_{597}$ is cultured using techniques known to those skilled in the art to produce a feline FcεRα protein PfelFc$_\epsilon$Rα$_{199}$.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated feline nucleic acid molecule selected from the group consisting of:
   (a) a feline nucleic acid molecule that encodes a protein that binds to IgE and hybridizes to a nucleic acid sequence selected from the group consisting of SEQ ID NO:3, SEQ ID NO:5, SEQ ID NO:8, SEQ ID NO:15 and SEQ ID NO:16 under hybridization and wash conditions which allow 30% or less base-pair mismatch, wherein such conditions are determined by a formula:

$T_m=81.5°$ C.$+16.6$ log M$+0.41$ (% G+C)$-500/n-0.61$ (% formamide), wherein $T_m$ represents the temperature at which two complementary nucleic acid molecule strands will disassociate, assuming 100% complementarity between the two strands, n represents the number of nucleotides in the shorter strand of the duplex being hybridized and log M represents the ionic strengths of the hybridization and wash solutions in moles/liter;
   wherein said wash is conducted at a temperature of $T_m$ minus 30° C.; and
   (b) a feline nucleic acid molecule fully complementary to a nucleic acid molecule of (a).

2. The isolated feline nucleic acid molecule of claim 1, wherein said feline nucleic acid molecule encodes a protein comprising an amino acid sequence selected from the group consisting of SEQ ID NO:2, SEQ ID NO:7, SEQ ID NO:12 and SEQ ID NO:13.

3. The isolated feline nucleic acid molecule of claim 1, wherein said nucleic acid molecule is selected from the group consisting of: (a) a feline nucleic acid molecule consisting of a coding strand with SEQ ID NO:1 and a complementary strand with SEQ ID NO:3 (nfelFc$_\epsilon$R$\alpha_{1069}$), (b) a feline nucleic acid molecule consisting of a coding strand with SEQ ID NO:4 and a complementary strand with SEQ ID NO:5 (nfelFc$_\epsilon$R$\alpha_{789}$), (c) a feline nucleic acid molecule consisting of a coding strand with SEQ ID NO:6 and a complementary strand with SEQ ID NO:8 (nfelFc$_\epsilon$R$\alpha_{714}$), (d) a feline nucleic acid molecule consisting of a coding strand with SEQ ID NO:11 and a complementary strand with SEQ ID NO:16 (nfelFc$_\epsilon$R$\alpha_{597}$) and (e) a nucleic acid molecule consisting of a coding strand with SEQ ID NO:14 and a complementary strand with SEQ ID NO:15 (nfelFc$_\epsilon$R$\alpha_{522}$).

4. The isolated feline nucleic acid molecule of claim 1, wherein said nucleic acid molecule comprises a nucleic acid sequence selected from the group consisting of SEQ ID NO:1, SEQ ID NO:4, SEQ ID NO:6, SEQ ID NO:11 and SEQ ID NO:14.

5. A recombinant molecule comprising a nucleic acid molecule as set forth in claim 1 operatively linked to a transcription control sequence.

6. A recombinant virus comprising a nucleic acid molecule as set forth in claim 1.

7. A recombinant cell comprising a nucleic acid molecule as set forth in claim 1.

8. An isolated nucleic acid molecule comprising a nucleic acid sequence selected from the group consisting of SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and SEQ ID NO:16.

9. The nucleic acid molecule of claim 8, wherein said nucleic acid molecule comprises a nucleic acid sequence selected from the group consisting of SEQ ID NO:6, SEQ ID NO:8, SEQ ID NO:11, SEQ ID NO:14, SEQ ID NO:15 and SEQ ID NO:16.

10. A method to produce a feline Fc$\epsilon$R$\alpha$ protein, said method comprising culturing a cell transformed with a feline nucleic acid molecule, wherein said feline nucleic acid molecule encodes a protein that binds to IgE and hybridizes to a nucleic acid sequence selected from the group consisting of SEQ ID NO:3, SEQ ID NO:5, SEQ ID NO:8, SEQ ID NO:15 and SEQ ID NO:16 under hybridization and wash conditions which allow 30% or less base-pair mismatch, wherein such conditions are determined by a formula:

$T_m=81.5°$ C.$+16.6$ log M$+0.41$(% G+C)$-500/n-0.61$(% formamide), wherein $T_m$ represents the temperature at which two complementary nucleic acid molecule strands will disassociate, assuming 100% complementarity between the two strands, n represents the number of nucleotides in the shorter strand of the duplex being hybridized and log M represents the ionic strengths of the hybridization and wash solutions in moles/liter;
wherein said wash is conducted at a temperature of $T_m$ minus 30° C.

11. The method of claim 10, wherein said nucleic acid molecule comprises a nucleic acid sequence selected from the group consisting of SEQ ID NO:1, SEQ ID NO:4, SEQ ID NO:6, SEQ ID NO:11 and SEQ ID NO:14.

12. The method of claim 10, wherein said nucleic acid molecule is selected from the group consisting of: (a) a feline nucleic acid molecule consisting of a coding strand with SEQ ID NO:1 and a complementary strand with SEQ ID NO:3 (nfelFc$_\epsilon$R$\alpha_{1069}$), (b) a feline nucleic acid molecule consisting of a coding strand with SEQ ID NO:4 and a complementary strand with SEQ ID NO:5 (nfelFc$_\epsilon$R$\alpha_{789}$), (c) a feline nucleic acid molecule consisting of a coding strand with SEQ ID NO:6 and a complementary strand with SEQ ID NO:8 (nfelFc$_\epsilon$R$\alpha_{714}$, (d) a feline nucleic acid molecule consisting of a coding strand with SEQ ID NO:11 and a complementary strand with SEQ ID NO:16 (nfelFc$_\epsilon$R$\alpha_{597}$) and (e) a nucleic acid molecule consisting of a coding strand with SEQ ID NO:14 and a complementary strand with SEQ ID NO:15 (nfelFc$_\epsilon$R$\alpha_{522}$).

13. The method of claim 10, wherein said transformed cell is *S. frugiperda*:pVL-nfelFc$_\epsilon$R$\alpha_{597}$, wherein nucleic acid molecule nfelFc$_\epsilon$R$\alpha_{597}$ consists of a coding strand with SEQ ID NO:11 and a complementary stand with SEQ ID NO:16.

14. A composition comprising an excipient and a feline nucleic acid molecule selected from the group consisting of:
   (a) a feline nucleic acid molecule that encodes a protein that binds to IgE and hybridizes to a nucleic acid sequence selected from the group consisting of SEQ ID NO:3, SEQ ID NO:5, SEQ ID NO:8, SEQ ID NO:15 and SEQ ID NO:16 under hybridization and wash conditions which allow 30% or less base-pair mismatch, wherein such conditions are determined by a formula:

$T_m=81.5°$ C.$+16.6$ log M$+0.41$(% G+C)$-500/n-0.61$(% formamide), wherein $T_m$ represents the temperature at which two complementary nucleic acid molecule strands will disassociate, assuming 100% complementarity between the two strands, n represents the number of nucleotides in the shorter strand of the duplex being hybridized and log M represents the ionic strengths of the hybridization and wash solutions in moles/liter;

wherein said wash is conducted at a temperature of $T_m$ minus 30° C.; and (b) a nucleic acid sequence fully complementary to a nucleic acid sequence of (a).

15. The composition of claim 14, wherein said composition further comprises a compound selected from the group consisting of an adjuvant and a carrier.

16. The composition of claim 14, wherein said feline nucleic acid molecule encodes a protein comprising an amino acid sequence selected from the group consisting of: SEQ ID NO:2, SEQ ID NO:7, SEQ ID NO:12 and SEQ ID NO:13.

17. The composition of claim 14, wherein said feline nucleic acid molecule comprises a nucleic acid sequence selected from the group consisting of: SEQ ID NO:1, SEQ ID NO:3, SEQ ID NO:4, SEQ ID NO:5, SEQ ID NO:6, SEQ ID NO:8, SEQ ID NO:11, SEQ ID NO:14, SEQ ID NO:15 and SEQ ID NO:16.

\* \* \* \* \*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1069 nucleotides
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 65..856

(xi) SEQUENCE DESCRIPTION: SEQ ID NO:1:

```
TTTAAGTCTA TTTTAAGGCG TTAGGTCTCT CCCGTCGGGT CGGCATTTGG GAGCCAGGGA        60

GGCG ATG CCG GTT TTC CTG GGA GGC CCT GCT CTG CTG TGG ACA GCA CTG       109
     Met Pro Val Phe Leu Gly Gly Pro Ala Leu Leu Trp Thr Ala Leu
      1               5                  10                  15

CTG CTC CTC CTC TAT CCA GAT GGC ATG TCA GCA GGC ACC CGG GAA CCT        157
Leu Leu Leu Leu Tyr Pro Asp Gly Met Ser Ala Gly Thr Arg Glu Pro
                 20                  25                  30

ACA GTG TCC TTG AAT CCA CCG TGG ACT ACC ATA TTG AAA GAA GAC AGT        205
Thr Val Ser Leu Asn Pro Pro Trp Thr Thr Ile Leu Lys Glu Asp Ser
             35                  40                  45

GTG ACT CTT ACA TGT AAA GAG AAC AAT TCT CTT GAA CTC AAC TCT ACT        253
Val Thr Leu Thr Cys Lys Glu Asn Asn Ser Leu Glu Leu Asn Ser Thr
         50                  55                  60
```

-continued

```
GTG TGG TTC CAC AAC AAG ACC AAG TTG GGA GTG ACA ACT TTA ACT TTG      301
Val Trp Phe His Asn Lys Thr Lys Leu Gly Val Thr Thr Leu Thr Leu
                 65                  70                  75

GAC ATC GTG AAA GCC CAA ATC CGC GAT AGT GGG GAA TAC ACG TGT CAG      349
Asp Ile Val Lys Ala Gln Ile Arg Asp Ser Gly Glu Tyr Thr Cys Gln
 80                  85                  90                  95

AAC AAA GGA TCC ATG CTG AGT AAA CCT GTG TCC TTA AAA GTC TTC CGT      397
Asn Lys Gly Ser Met Leu Ser Lys Pro Val Ser Leu Lys Val Phe Arg
                    100                 105                 110

GAG TGG CTG CTC CTT CAG GCC TCT ACT GAG GTG GTG CTG GAG GGT GAG      445
Glu Trp Leu Leu Leu Gln Ala Ser Thr Glu Val Val Leu Glu Gly Glu
                115                 120                 125

TCC TTC CTC ATC AGG TGC CAC AGT TGG AGG AAT TTG AAT GTC AAA AAA      493
Ser Phe Leu Ile Arg Cys His Ser Trp Arg Asn Leu Asn Val Lys Lys
                130                 135                 140

GTG ACC TAC TAC AGG AAT GGC AAG TTC CTC CAG TTC TGG TAC GAC AAC      541
Val Thr Tyr Tyr Arg Asn Gly Lys Phe Leu Gln Phe Trp Tyr Asp Asn
            145                 150                 155

TAC AAC ATC ACC ATT AAC AAT GCC ACA GAA ACA GAC AGC GGC ACC TAC      589
Tyr Asn Ile Thr Ile Asn Asn Ala Thr Glu Thr Asp Ser Gly Thr Tyr
160                 165                 170                 175

TAC TGC ACG GGC TGG ATT TCG AGG CAA AAT CAC ATC TCT AAC TTC CTC      637
Tyr Cys Thr Gly Trp Ile Ser Arg Gln Asn His Ile Ser Asn Phe Leu
                180                 185                 190

AAC ATC GTT GTG AGA AAA GAT TCC CCT CCG GAG CAC CAA AGC AAA TAC      685
Asn Ile Val Val Arg Lys Asp Ser Pro Pro Glu His Gln Ser Lys Tyr
                195                 200                 205

TAC TGG CTA CAA TTT GTG ATC CCA TCG TTG GTG GTG CTT CTG TTT GCT      733
Tyr Trp Leu Gln Phe Val Ile Pro Ser Leu Val Val Leu Leu Phe Ala
            210                 215                 220

GCG GAC ACG GGG CTG TTT ATC TCG ACC CAG CAG CAG CTG ACC CTG CTC      781
Ala Asp Thr Gly Leu Phe Ile Ser Thr Gln Gln Gln Leu Thr Leu Leu
        225                 230                 235

TTG AAG ATT AAG ACG ACC AGG AGG AGC AGG AAC CTT ATG GAC CCA CGT      829
Leu Lys Ile Lys Thr Thr Arg Arg Ser Arg Asn Leu Met Asp Pro Arg
240                 245                 250                 255

CCC AAG CCA GAC CCC AAA AAG AAC TGA TGTTGCTGCT TGGGAAACAT            876
Pro Lys Pro Asp Pro Lys Lys Asn
                    260

TTGCAACGGC AACCTCTTTC TGGCATCAGC GATTGCTTCT CCGTGGTCAA ACACAGCTCG    936

CAACGCACAC AGGAGCGTCT GGACGCAAGG CTTTAACAGA CCTGCTTCAT TAAGCCAGCT    996

GAAACTGGTT ACATGGCATG TAACAACAAG GGCTCAATAA ACATCACTTA AACAAAAAAA    1056

AAAAAAAAAA AAA                                                       1069
```

(2) INFORMATION FOR SEQ ID NO:2:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Val Phe Leu Gly Gly Pro Ala Leu Leu Trp Thr Ala Leu Leu
 1               5                  10                  15

Leu Leu Leu Tyr Pro Asp Gly Met Ser Ala Gly Thr Arg Glu Pro Thr
            20                  25                  30
```

Val Ser Leu Asn Pro Pro Trp Thr Thr Ile Leu Lys Glu Asp Ser Val
        35                  40                  45

Thr Leu Thr Cys Lys Glu Asn Asn Ser Leu Glu Leu Asn Ser Thr Val
        50                  55                  60

Trp Phe His Asn Lys Thr Lys Leu Gly Val Thr Thr Leu Thr Leu Asp
65                  70                  75                  80

Ile Val Lys Ala Gln Ile Arg Asp Ser Gly Glu Tyr Thr Cys Gln Asn
                85                  90                  95

Lys Gly Ser Met Leu Ser Lys Pro Val Ser Leu Lys Val Phe Arg Glu
            100                 105                 110

Trp Leu Leu Gln Ala Ser Thr Glu Val Val Leu Glu Gly Glu Ser
        115                 120                 125

Phe Leu Ile Arg Cys His Ser Trp Arg Asn Leu Asn Val Lys Lys Val
        130                 135                 140

Thr Tyr Tyr Arg Asn Gly Lys Phe Leu Gln Phe Trp Tyr Asp Asn Tyr
145                 150                 155                 160

Asn Ile Thr Ile Asn Asn Ala Thr Glu Thr Asp Ser Gly Thr Tyr Tyr
                165                 170                 175

Cys Thr Gly Trp Ile Ser Arg Gln Asn His Ile Ser Asn Phe Leu Asn
            180                 185                 190

Ile Val Val Arg Lys Asp Ser Pro Pro Glu His Gln Ser Lys Tyr Tyr
        195                 200                 205

Trp Leu Gln Phe Val Ile Pro Ser Leu Val Val Leu Leu Phe Ala Ala
        210                 215                 220

Asp Thr Gly Leu Phe Ile Ser Thr Gln Gln Gln Leu Thr Leu Leu Leu
225                 230                 235                 240

Lys Ile Lys Thr Thr Arg Arg Ser Arg Asn Leu Met Asp Pro Arg Pro
                245                 250                 255

Lys Pro Asp Pro Lys Lys Asn
            260

(2) INFORMATION FOR SEQ ID NO:3:

(i) SEQUENCE CHARACTERISTICS:
        (A) LENGTH: 1069 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TTTTTTTTTT TTTTTTTTTT GTTTAAGTGA TGTTTATTGA GCCCTTGTTG TTACATGCCA        60

TGTAACCAGT TTCAGCTGGC TTAATGAAGC AGGTCTGTTA AAGCCTTGCG TCCAGACGCT       120

CCTGTGTGCG TTGCGAGCTG TGTTTGACCA CGGAGAAGCA ATCGCTGATG CCAGAAAGAG       180

GTTGCCGTTG CAAATGTTTC CAAGCAGCA ACATCAGTTC TTTTTGGGGT CTGGCTTGGG        240

ACGTGGGTCC ATAAGGTTCC TGCTCCTCCT GGTCGTCTTA ATCTTCAAGA GCAGGGTCAG       300

CTGCTGCTGG GTCGAGATAA ACAGCCCCGT GTCCGCAGCA AACAGAAGCA CCACCAACGA       360

TGGGATCACA AATTGTAGCC AGTAGTATTT GCTTTGGTGC TCCGGAGGGG AATCTTTTCT       420

CACAACGATG TTGAGGAAGT TAGAGATGTG ATTTTGCCTC GAAATCCAGC CCGTGCAGTA       480

GTAGGTGCCG CTGTCTGTTT CTGTGGCATT GTTAATGGTG ATGTTGTAGT TGTCGTACCA       540

GAACTGGAGG AACTTGCCAT TCCTGTAGTA GGTCACTTTT TTGACATTCA AATTCCTCCA       600

ACTGTGGCAC CTGATGAGGA AGGACTCACC CTCCAGCACC ACCTCAGTAG AGGCCTGAAG       660

```
GAGCAGCCAC TCACGGAAGA CTTTTAAGGA CACAGGTTTA CTCAGCATGG ATCCTTTGTT      720

CTGACACGTG TATTCCCCAC TATCGCGGAT TTGGGCTTTC ACGATGTCCA AAGTTAAAGT      780

TGTCACTCCC AACTTGGTCT TGTTGTGGAA CCACACAGTA GAGTTGAGTT CAAGAGAATT      840

GTTCTCTTTA CATGTAAGAG TCACACTGTC TTCTTTCAAT ATGGTAGTCC ACGGTGGATT      900

CAAGGACACT GTAGGTTCCC GGGTGCCTGC TGACATGCCA TCTGGATAGA GGAGGAGCAG      960

CAGTGCTGTC CACAGCAGAG CAGGGCCTCC CAGGAAAACC GGCATCGCCT CCCTGGCTCC     1020

CAAATGCCGA CCCGACGGGA GAGACCTAAC GCCTTAAAAT AGACTTAAA                 1069
```

(2) INFORMATION FOR SEQ ID NO:4:

(i) SEQUENCE CHARACTERISTICS:
        (A) LENGTH: 789 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..789

(xi) SEQUENCE DESCRIPTION: SEQ ID NO:4:

```
ATG CCG GTT TTC CTG GGA GGC CCT GCT CTG CTG TGG ACA GCA CTG CTG        48
Met Pro Val Phe Leu Gly Gly Pro Ala Leu Leu Trp Thr Ala Leu Leu
 1               5                  10                  15

CTC CTC CTC TAT CCA GAT GGC ATG TCA GCA GGC ACC CGG GAA CCT ACA        96
Leu Leu Leu Tyr Pro Asp Gly Met Ser Ala Gly Thr Arg Glu Pro Thr
                 20                  25                  30

GTG TCC TTG AAT CCA CCG TGG ACT ACC ATA TTG AAA GAA GAC AGT GTG       144
Val Ser Leu Asn Pro Pro Trp Thr Thr Ile Leu Lys Glu Asp Ser Val
             35                  40                  45

ACT CTT ACA TGT AAA GAG AAC AAT TCT CTT GAA CTC AAC TCT ACT GTG       192
Thr Leu Thr Cys Lys Glu Asn Asn Ser Leu Glu Leu Asn Ser Thr Val
         50                  55                  60

TGG TTC CAC AAC AAG ACC AAG TTG GGA GTG ACA ACT TTA ACT TTG GAC       240
Trp Phe His Asn Lys Thr Lys Leu Gly Val Thr Thr Leu Thr Leu Asp
 65                  70                  75                  80

ATC GTG AAA GCC CAA ATC CGC GAT AGT GGG GAA TAC ACG TGT CAG AAC       288
Ile Val Lys Ala Gln Ile Arg Asp Ser Gly Glu Tyr Thr Cys Gln Asn
                 85                  90                  95

AAA GGA TCC ATG CTG AGT AAA CCT GTG TCC TTA AAA GTC TTC CGT GAG       336
Lys Gly Ser Met Leu Ser Lys Pro Val Ser Leu Lys Val Phe Arg Glu
             100                 105                 110

TGG CTG CTC CTT CAG GCC TCT ACT GAG GTG GTG CTG GAG GGT GAG TCC       384
Trp Leu Leu Leu Gln Ala Ser Thr Glu Val Val Leu Glu Gly Glu Ser
         115                 120                 125

TTC CTC ATC AGG TGC CAC AGT TGG AGG AAT TTG AAT GTC AAA AAA GTG       432
Phe Leu Ile Arg Cys His Ser Trp Arg Asn Leu Asn Val Lys Lys Val
     130                 135                 140

ACC TAC TAC AGG AAT GGC AAG TTC CTC CAG TTC TGG TAC GAC AAC TAC       480
Thr Tyr Tyr Arg Asn Gly Lys Phe Leu Gln Phe Trp Tyr Asp Asn Tyr
145                 150                 155

AAC ATC ACC ATT AAC AAT GCC ACA GAA ACA GAC AGC GGC ACC TAC TAC       528
Asn Ile Thr Ile Asn Asn Ala Thr Glu Thr Asp Ser Gly Thr Tyr Tyr
160                 165                 170                 175

TGC ACG GGC TGG ATT TCG AGG CAA AAT CAC ATC TCT AAC TTC CTC AAC       576
Cys Thr Gly Trp Ile Ser Arg Gln Asn His Ile Ser Asn Phe Leu Asn
                 180                 185                 190
```

```
ATC GTT GTG AGA AAA GAT TCC CCT CCG GAG CAC CAA AGC AAA TAC TAC      624
Ile Val Val Arg Lys Asp Ser Pro Pro Glu His Gln Ser Lys Tyr Tyr
            195                 200                 205

TGG CTA CAA TTT GTG ATC CCA TCG TTG GTG GTG CTT CTG TTT GCT GCG      672
Trp Leu Gln Phe Val Ile Pro Ser Leu Val Val Leu Leu Phe Ala Ala
            210                 215                 220

GAC ACG GGG CTG TTT ATC TCG ACC CAG CAG CAG CTG ACC CTG CTC TTG      720
Asp Thr Gly Leu Phe Ile Ser Thr Gln Gln Gln Leu Thr Leu Leu Leu
225                 230                 235

AAG ATT AAG ACG ACC AGG AGG AGC AGG AAC CTT ATG GAC CCA CGT CCC      768
Lys Ile Lys Thr Thr Arg Arg Ser Arg Asn Leu Met Asp Pro Arg Pro
240                 245                 250                 255

AAG CCA GAC CCC AAA AAG AAC                                          789
Lys Pro Asp Pro Lys Lys Asn
                260
```

(2) INFORMATION FOR SEQ ID NO:5:

(i) SEQUENCE CHARACTERISTICS:
        (A) LENGTH: 789 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTTCTTTTTG GGGTCTGGCT TGGGACGTGG GTCCATAAGG TTCCTGCTCC TCCTGGTCGT     60

CTTAATCTTC AAGAGCAGGG TCAGCTGCTG CTGGGTCGAG ATAAACAGCC CCGTGTCCGC    120

AGCAAACAGA AGCACCACCA ACGATGGGAT CACAAATTGT AGCCAGTAGT ATTTGCTTTG    180

GTGCTCCGGA GGGGAATCTT TTCTCACAAC GATGTTGAGG AAGTTAGAGA TGTGATTTTG    240

CCTCGAAATC CAGCCCGTGC AGTAGTAGGT GCCGCTGTCT GTTTCTGTGG CATTGTTAAT    300

GGTGATGTTG TAGTTGTCGT ACCAGAACTG GAGGAACTTG CCATTCCTGT AGTAGGTCAC    360

TTTTTTGACA TTCAAATTCC TCCAACTGTG GCACCTGATG AGGAAGGACT CACCCTCCAG    420

CACCACCTCA GTAGAGGCCT GAAGGAGCAG CCACTCACGG AAGACTTTTA AGGACACAGG    480

TTTACTCAGC ATGGATCCTT TGTTCTGACA CGTGTATTCC CCACTATCGC GGATTTGGGC    540

TTTCACGATG TCCAAAGTTA AAGTTGTCAC TCCCAACTTG GTCTTGTTGT GGAACCACAC    600

AGTAGAGTTG AGTTCAAGAG AATTGTTCTC TTTACATGTA AGAGTCACAC TGTCTTCTTT    660

CAATATGGTA GTCCACGGTG GATTCAAGGA CACTGTAGGT TCCCGGGTGC CTGCTGACAT    720

GCCATCTGGA TAGAGGAGGA GCAGCAGTGC TGTCCACAGC AGAGCAGGGC CTCCCAGGAA    780

AACCGGCAT                                                           789
```

(2) INFORMATION FOR SEQ ID NO:6:

(i) SEQUENCE CHARACTERISTICS:
        (A) LENGTH: 714 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..714

(xi) SEQUENCE DESCRIPTION: SEQ ID NO:6:

```
GCA GGC ACC CGG GAA CCT ACA GTG TCC TTG AAT CCA CCG TGG ACT ACC        48
Ala Gly Thr Arg Glu Pro Thr Val Ser Leu Asn Pro Pro Trp Thr Thr
 1               5                  10                  15

ATA TTG AAA GAA GAC AGT GTG ACT CTT ACA TGT AAA GAG AAC AAT TCT        96
Ile Leu Lys Glu Asp Ser Val Thr Leu Thr Cys Lys Glu Asn Asn Ser
                 20                  25                  30

CTT GAA CTC AAC TCT ACT GTG TGG TTC CAC AAC AAG ACC AAG TTG GGA       144
Leu Glu Leu Asn Ser Thr Val Trp Phe His Asn Lys Thr Lys Leu Gly
             35                  40                  45

GTG ACA ACT TTA ACT TTG GAC ATC GTG AAA GCC CAA ATC CGC GAT AGT       192
Val Thr Thr Leu Thr Leu Asp Ile Val Lys Ala Gln Ile Arg Asp Ser
         50                  55                  60

GGG GAA TAC ACG TGT CAG AAC AAA GGA TCC ATG CTG AGT AAA CCT GTG       240
Gly Glu Tyr Thr Cys Gln Asn Lys Gly Ser Met Leu Ser Lys Pro Val
65                   70                  75                  80

TCC TTA AAA GTC TTC CGT GAG TGG CTG CTC CTT CAG GCC TCT ACT GAG       288
Ser Leu Lys Val Phe Arg Glu Trp Leu Leu Leu Gln Ala Ser Thr Glu
                 85                  90                  95

GTG GTG CTG GAG GGT GAG TCC TTC CTC ATC AGG TGC CAC AGT TGG AGG       336
Val Val Leu Glu Gly Glu Ser Phe Leu Ile Arg Cys His Ser Trp Arg
            100                 105                 110

AAT TTG AAT GTC AAA AAA GTG ACC TAC TAC AGG AAT GGC AAG TTC CTC       384
Asn Leu Asn Val Lys Lys Val Thr Tyr Tyr Arg Asn Gly Lys Phe Leu
        115                 120                 125

CAG TTC TGG TAC GAC AAC TAC AAC ATC ACC ATT AAC AAT GCC ACA GAA       432
Gln Phe Trp Tyr Asp Asn Tyr Asn Ile Thr Ile Asn Asn Ala Thr Glu
    130                 135                 140

ACA GAC AGC GGC ACC TAC TAC TGC ACG GGC TGG ATT TCG AGG CAA AAT       480
Thr Asp Ser Gly Thr Tyr Tyr Cys Thr Gly Trp Ile Ser Arg Gln Asn
145                 150                 155                 160

CAC ATC TCT AAC TTC CTC AAC ATC GTT GTG AGA AAA GAT TCC CCT CCG       528
His Ile Ser Asn Phe Leu Asn Ile Val Val Arg Lys Asp Ser Pro Pro
                165                 170                 175

GAG CAC CAA AGC AAA TAC TAC TGG CTA CAA TTT GTG ATC CCA TCG TTG       576
Glu His Gln Ser Lys Tyr Tyr Trp Leu Gln Phe Val Ile Pro Ser Leu
            180                 185                 190

GTG GTG CTT CTG TTT GCT GCG GAC ACG GGG CTG TTT ATC TCG ACC CAG       624
Val Val Leu Leu Phe Ala Ala Asp Thr Gly Leu Phe Ile Ser Thr Gln
        195                 200                 205

CAG CAG CTG ACC CTG CTC TTG AAG ATT AAG ACG ACC AGG AGG AGC AGG       672
Gln Gln Leu Thr Leu Leu Leu Lys Ile Lys Thr Thr Arg Arg Ser Arg
    210                 215                 220

AAC CTT ATG GAC CCA CGT CCC AAG CCA GAC CCC AAA AAG AAC               714
Asn Leu Met Asp Pro Arg Pro Lys Pro Asp Pro Lys Lys Asn
225                 230                 235
```

(2) INFORMATION FOR SEQ ID NO:7:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:7:

```
Ala Gly Thr Arg Glu Pro Thr Val Ser Leu Asn Pro Pro Trp Thr Thr
 1               5                  10                  15

Ile Leu Lys Glu Asp Ser Val Thr Leu Thr Cys Lys Glu Asn Asn Ser
                 20                  25                  30

Leu Glu Leu Asn Ser Thr Val Trp Phe His Asn Lys Thr Lys Leu Gly
```

```
                35                    40                     45
Val Thr Thr Leu Thr Leu Asp Ile Val Lys Ala Gln Ile Arg Asp Ser
    50                    55                    60
Gly Glu Tyr Thr Cys Gln Asn Lys Gly Ser Met Leu Ser Lys Pro Val
65                    70                    75                    80
Ser Leu Lys Val Phe Arg Glu Trp Leu Leu Leu Gln Ala Ser Thr Glu
                85                    90                    95
Val Val Leu Glu Gly Glu Ser Phe Leu Ile Arg Cys His Ser Trp Arg
                100                   105                   110
Asn Leu Asn Val Lys Lys Val Thr Tyr Tyr Arg Asn Gly Lys Phe Leu
            115                   120                   125
Gln Phe Trp Tyr Asp Asn Tyr Asn Ile Thr Ile Asn Asn Ala Thr Glu
        130                   135                   140
Thr Asp Ser Gly Thr Tyr Tyr Cys Thr Gly Trp Ile Ser Arg Gln Asn
145                   150                   155                   160
His Ile Ser Asn Phe Leu Asn Ile Val Val Arg Lys Asp Ser Pro Pro
                165                   170                   175
Glu His Gln Ser Lys Tyr Tyr Trp Leu Gln Phe Val Ile Pro Ser Leu
                180                   185                   190
Val Val Leu Leu Phe Ala Ala Asp Thr Gly Leu Phe Ile Ser Thr Gln
            195                   200                   205
Gln Gln Leu Thr Leu Leu Lys Ile Lys Thr Thr Arg Arg Ser Arg
        210                   215                   220
Asn Leu Met Asp Pro Arg Pro Lys Pro Asp Pro Lys Lys Asn
225                   230                   235
```

(2) INFORMATION FOR SEQ ID NO:8:

(i) SEQUENCE CHARACTERISTICS:
        (A) LENGTH: 714 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GTTCTTTTTG GGGTCTGGCT TGGGACGTGG GTCCATAAGG TTCCTGCTCC TCCTGGTCGT    60
CTTAATCTTC AAGAGCAGGG TCAGCTGCTG CTGGGTCGAG ATAAACAGCC CCGTGTCCGC   120
AGCAAACAGA AGCACCACCA ACGATGGGAT CACAAATTGT AGCCAGTAGT ATTTGCTTTG   180
GTGCTCCGGA GGGGAATCTT TTCTCACAAC GATGTTGAGG AAGTTAGAGA TGTGATTTTG   240
CCTCGAAATC CAGCCCGTGC AGTAGTAGGT GCCGCTGTCT GTTTCTGTGG CATTGTTAAT   300
GGTGATGTTG TAGTTGTCGT ACCAGAACTG GAGGAACTTG CCATTCCTGT AGTAGGTCAC   360
TTTTTTGACA TTCAAATTCC TCCAACTGTG GCACCTGATG AGGAAGGACT CACCCTCCAG   420
CACCACCTCA GTAGAGGCCT GAAGGAGCAG CCACTCACGG AAGACTTTTA AGGACACAGG   480
TTTACTCAGC ATGGATCCTT TGTTCTGACA CGTGTATTCC CCACTATCGC GGATTTGGGC   540
TTTCACGATG TCCAAAGTTA AAGTTGTCAC TCCCAACTTG GTCTTGTTGT GGAACCACAC   600
AGTAGAGTTG AGTTCAAGAG AATTGTTCTC TTTACATGTA AGAGTCACAC TGTCTTCTTT   660
CAATATGGTA GTCCACGGTG GATTCAAGGA CACTGTAGGT TCCCGGGTGC CTGC          714
```

(2) INFORMATION FOR SEQ ID NO:9:

(i) SEQUENCE CHARACTERISTICS:

-continued (A) LENGTH: 42 bases
(B) TYPE: nucleic acid
(C) STRANDEDNESS: single
(D) TOPOLOGY: linear (ii) MOLECULE TYPE: primer (xi) SEQUENCE DESCRIPTION: SEQ ID NO:9:

CGCGAATTCT ATAAATATGC CGGTTTTCCT GGGAGGCCCT GC                                42

(2) INFORMATION FOR SEQ ID NO:10:

(i) SEQUENCE CHARACTERISTICS:
(A) LENGTH: 40 bases
(B) TYPE: nucleic acid
(C) STRANDEDNESS: single
(D) TOPOLOGY: linear (ii) MOLECULE TYPE: primer (xi) SEQUENCE DESCRIPTION: SEQ ID NO:10:

GCGAGATCTT TAGGAATCTT TTCTCACAAC GATGTTGAGG                                   40

(2) INFORMATION FOR SEQ ID NO:11:

(i) SEQUENCE CHARACTERISTICS:
(A) LENGTH: 597 nucleotides
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..597

(xi) SEQUENCE DESCRIPTION: SEQ ID NO:11:

```
ATG CCG GTT TTC CTG GGA GGC CCT GCT CTG CTG TGG ACA GCA CTG CTG         48
Met Pro Val Phe Leu Gly Gly Pro Ala Leu Leu Trp Thr Ala Leu Leu
 1               5                  10                  15

CTC CTC CTC TAT CCA GAT GGC ATG TCA GCA GGC ACC CGG GAA CCT ACA         96
Leu Leu Leu Tyr Pro Asp Gly Met Ser Ala Gly Thr Arg Glu Pro Thr
                20                  25                  30

GTG TCC TTG AAT CCA CCG TGG ACT ACC ATA TTG AAA GAA GAC AGT GTG        144
Val Ser Leu Asn Pro Pro Trp Thr Thr Ile Leu Lys Glu Asp Ser Val
            35                  40                  45

ACT CTT ACA TGT AAA GAG AAC AAT TCT CTT GAA CTC AAC TCT ACT GTG        192
Thr Leu Thr Cys Lys Glu Asn Asn Ser Leu Glu Leu Asn Ser Thr Val
        50                  55                  60

TGG TTC CAC AAC AAG ACC AAG TTG GGA GTG ACA ACT TTA ACT TTG GAC        240
Trp Phe His Asn Lys Thr Lys Leu Gly Val Thr Thr Leu Thr Leu Asp
65                  70                  75                  80

ATC GTG AAA GCC CAA ATC CGC GAT AGT GGG GAA TAC ACG TGT CAG AAC        288
Ile Val Lys Ala Gln Ile Arg Asp Ser Gly Glu Tyr Thr Cys Gln Asn
                85                  90                  95

AAA GGA TCC ATG CTG AGT AAA CCT GTG TCC TTA AAA GTC TTC CGT GAG        336
Lys Gly Ser Met Leu Ser Lys Pro Val Ser Leu Lys Val Phe Arg Glu
            100                 105                 110

TGG CTG CTC CTT CAG GCC TCT ACT GAG GTG GTG CTG GAG GGT GAG TCC        384
Trp Leu Leu Leu Gln Ala Ser Thr Glu Val Val Leu Glu Gly Glu Ser
        115                 120                 125

TTC CTC ATC AGG TGC CAC AGT TGG AGG AAT TTG AAT GTC AAA AAA GTG        432
Phe Leu Ile Arg Cys His Ser Trp Arg Asn Leu Asn Val Lys Lys Val
    130                 135                 140
```

```
ACC TAC TAC AGG AAT GGC AAG TTC CTC CAG TTC TGG TAC GAC AAC TAC     480
Thr Tyr Tyr Arg Asn Gly Lys Phe Leu Gln Phe Trp Tyr Asp Asn Tyr
145                 150                 155                 160

AAC ATC ACC ATT AAC AAT GCC ACA GAA ACA GAC AGC GGC ACC TAC TAC     528
Asn Ile Thr Ile Asn Asn Ala Thr Glu Thr Asp Ser Gly Thr Tyr Tyr
                165                 170                 175

TGC ACG GGC TGG ATT TCG AGG CAA AAT CAC ATC TCT AAC TTC CTC AAC     576
Cys Thr Gly Trp Ile Ser Arg Gln Asn His Ile Ser Asn Phe Leu Asn
            180                 185                 190

ATC GTT GTG AGA AAA GAT TCC                                         597
Ile Val Val Arg Lys Asp Ser
        195
```

(2) INFORMATION FOR SEQ ID NO:12:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:12:

```
Met Pro Val Phe Leu Gly Gly Pro Ala Leu Leu Trp Thr Ala Leu Leu
1               5                   10                  15

Leu Leu Leu Tyr Pro Asp Gly Met Ser Ala Gly Thr Arg Glu Pro Thr
                20                  25                  30

Val Ser Leu Asn Pro Pro Trp Thr Thr Ile Leu Lys Glu Asp Ser Val
            35                  40                  45

Thr Leu Thr Cys Lys Glu Asn Asn Ser Leu Glu Leu Asn Ser Thr Val
        50                  55                  60

Trp Phe His Asn Lys Thr Lys Leu Gly Val Thr Thr Leu Thr Leu Asp
65                  70                  75                  80

Ile Val Lys Ala Gln Ile Arg Asp Ser Gly Glu Tyr Thr Cys Gln Asn
                85                  90                  95

Lys Gly Ser Met Leu Ser Lys Pro Val Ser Leu Lys Val Phe Arg Glu
                100                 105                 110

Trp Leu Leu Leu Gln Ala Ser Thr Glu Val Val Leu Glu Gly Glu Ser
            115                 120                 125

Phe Leu Ile Arg Cys His Ser Trp Arg Asn Leu Asn Val Lys Lys Val
        130                 135                 140

Thr Tyr Tyr Arg Asn Gly Lys Phe Leu Gln Phe Trp Tyr Asp Asn Tyr
145                 150                 155                 160

Asn Ile Thr Ile Asn Asn Ala Thr Glu Thr Asp Ser Gly Thr Tyr Tyr
                165                 170                 175

Cys Thr Gly Trp Ile Ser Arg Gln Asn His Ile Ser Asn Phe Leu Asn
            180                 185                 190

Ile Val Val Arg Lys Asp Ser
        195
```

(2) INFORMATION FOR SEQ ID NO:13:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:13:

```
Ala Gly Thr Arg Glu Pro Thr Val Ser Leu Asn Pro Pro Trp Thr Thr
 1               5                  10                  15

Ile Leu Lys Glu Asp Ser Val Thr Leu Thr Cys Lys Glu Asn Asn Ser
                20                  25                  30

Leu Glu Leu Asn Ser Thr Val Trp Phe His Asn Lys Thr Lys Leu Gly
            35                  40                  45

Val Thr Thr Leu Thr Leu Asp Ile Val Lys Ala Gln Ile Arg Asp Ser
        50                  55                  60

Gly Glu Tyr Thr Cys Gln Asn Lys Gly Ser Met Leu Ser Lys Pro Val
 65                  70                  75                  80

Ser Leu Lys Val Phe Arg Glu Trp Leu Leu Leu Gln Ala Ser Thr Glu
                85                  90                  95

Val Val Leu Glu Gly Glu Ser Phe Leu Ile Arg Cys His Ser Trp Arg
            100                 105                 110

Asn Leu Asn Val Lys Lys Val Thr Tyr Tyr Arg Asn Gly Lys Phe Leu
        115                 120                 125

Gln Phe Trp Tyr Asp Asn Tyr Asn Ile Thr Ile Asn Asn Ala Thr Glu
130                 135                 140

Thr Asp Ser Gly Thr Tyr Tyr Cys Thr Gly Trp Ile Ser Arg Gln Asn
145                 150                 155                 160

His Ile Ser Asn Phe Leu Asn Ile Val Val Arg Lys Asp Ser
                165                 170
```

(2) INFORMATION FOR SEQ ID NO:14:

(i) SEQUENCE CHARACTERISTICS:
        (A) LENGTH: 522 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..522

(xi) SEQUENCE DESCRIPTION: SEQ ID NO:14:

```
GCA GGC ACC CGG GAA CCT ACA GTG TCC TTG AAT CCA CCG TGG ACT ACC        48
Ala Gly Thr Arg Glu Pro Thr Val Ser Leu Asn Pro Pro Trp Thr Thr
 1               5                  10                  15

ATA TTG AAA GAA GAC AGT GTG ACT CTT ACA TGT AAA GAG AAC AAT TCT        96
Ile Leu Lys Glu Asp Ser Val Thr Leu Thr Cys Lys Glu Asn Asn Ser
                20                  25                  30

CTT GAA CTC AAC TCT ACT GTG TGG TTC CAC AAC AAG ACC AAG TTG GGA       144
Leu Glu Leu Asn Ser Thr Val Trp Phe His Asn Lys Thr Lys Leu Gly
            35                  40                  45

GTG ACA ACT TTA ACT TTG GAC ATC GTG AAA GCC CAA ATC CGC GAT AGT       192
Val Thr Thr Leu Thr Leu Asp Ile Val Lys Ala Gln Ile Arg Asp Ser
        50                  55                  60

GGG GAA TAC ACG TGT CAG AAC AAA GGA TCC ATG CTG AGT AAA CCT GTG       240
Gly Glu Tyr Thr Cys Gln Asn Lys Gly Ser Met Leu Ser Lys Pro Val
 65                  70                  75                  80

TCC TTA AAA GTC TTC CGT GAG TGG CTG CTC CTT CAG GCC TCT ACT GAG       288
Ser Leu Lys Val Phe Arg Glu Trp Leu Leu Leu Gln Ala Ser Thr Glu
                85                  90                  95

GTG GTG CTG GAG GGT GAG TCC TTC CTC ATC AGG TGC CAC AGT TGG AGG       336
Val Val Leu Glu Gly Glu Ser Phe Leu Ile Arg Cys His Ser Trp Arg
            100                 105                 110

AAT TTG AAT GTC AAA AAA GTG ACC TAC TAC AGG AAT GGC AAG TTC CTC       384
```

```
Asn Leu Asn Val Lys Lys Val Thr Tyr Tyr Arg Asn Gly Lys Phe Leu
        115                 120                 125
CAG TTC TGG TAC GAC AAC TAC AAC ATC ACC ATT AAC AAT GCC ACA GAA        432
Gln Phe Trp Tyr Asp Asn Tyr Asn Ile Thr Ile Asn Asn Ala Thr Glu
    130                 135                 140
ACA GAC AGC GGC ACC TAC TAC TGC ACG GGC TGG ATT TCG AGG CAA AAT        480
Thr Asp Ser Gly Thr Tyr Tyr Cys Thr Gly Trp Ile Ser Arg Gln Asn
145                 150                 155                 160
CAC ATC TCT AAC TTC CTC AAC ATC GTT GTG AGA AAA GAT TCC                522
His Ile Ser Asn Phe Leu Asn Ile Val Val Arg Lys Asp Ser
                165                 170
```

(2) INFORMATION FOR SEQ ID NO:15:

(i) SEQUENCE CHARACTERISTICS:
        (A) LENGTH: 522 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
GGAATCTTTT CTCACAACGA TGTTGAGGAA GTTAGAGATG TGATTTTGCC TCGAAATCCA        60
GCCCGTGCAG TAGTAGGTGC CGCTGTCTGT TTCTGTGGCA TTGTTAATGG TGATGTTGTA       120
GTTGTCGTAC CAGAACTGGA GGAACTTGCC ATTCCTGTAG TAGGTCACTT TTTTGACATT       180
CAAATTCCTC CAACTGTGGC ACCTGATGAG GAAGGACTCA CCCTCCAGCA CCACCTCAGT       240
AGAGGCCTGA AGGAGCAGCC ACTCACGGAA GACTTTTAAG GACACAGGTT TACTCAGCAT       300
GGATCCTTTG TTCTGACACG TGTATTCCCC ACTATCGCGG ATTTGGGCTT TCACGATGTC       360
CAAAGTTAAA GTTGTCACTC CCAACTTGGT CTTGTTGTGG AACCACACAG TAGAGTTGAG       420
TTCAAGAGAA TTGTTCTCTT TACATGTAAG AGTCACACTG TCTTCTTTCA ATATGGTAGT       480
CCACGGTGGA TTCAAGGACA CTGTAGGTTC CCGGGTGCCT GC                         522
```

(2) INFORMATION FOR SEQ ID NO:16:

(i) SEQUENCE CHARACTERISTICS:
        (A) LENGTH: 597 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GGAATCTTTT CTCACAACGA TGTTGAGGAA GTTAGAGATG TGATTTTGCC TCGAAATCCA        60
GCCCGTGCAG TAGTAGGTGC CGCTGTCTGT TTCTGTGGCA TTGTTAATGG TGATGTTGTA       120
GTTGTCGTAC CAGAACTGGA GGAACTTGCC ATTCCTGTAG TAGGTCACTT TTTTGACATT       180
CAAATTCCTC CAACTGTGGC ACCTGATGAG GAAGGACTCA CCCTCCAGCA CCACCTCAGT       240
AGAGGCCTGA AGGAGCAGCC ACTCACGGAA GACTTTTAAG GACACAGGTT TACTCAGCAT       300
GGATCCTTTG TTCTGACACG TGTATTCCCC ACTATCGCGG ATTTGGGCTT TCACGATGTC       360
CAAAGTTAAA GTTGTCACTC CCAACTTGGT CTTGTTGTGG AACCACACAG TAGAGTTGAG       420
TTCAAGAGAA TTGTTCTCTT TACATGTAAG AGTCACACTG TCTTCTTTCA ATATGGTAGT       480
CCACGGTGGA TTCAAGGACA CTGTAGGTTC CCGGGTGCCT GCTGACATGC CATCTGGATA       540
GAGGAGGAGC AGCAGTGCTG TCCACAGCAG AGCAGGGCCT CCCAGGAAAA CCGGCAT          597
```